United States Patent
Holmes et al.

(10) Patent No.: US 12,054,791 B2
(45) Date of Patent: Aug. 6, 2024

(54) PATHOGEN AND ANTIMICROBIAL RESISTANCE TESTING

(71) Applicant: Labrador Diagnostics LLC, Healdsburg, CA (US)

(72) Inventors: Elizabeth A. Holmes, San Francisco, CA (US); Chandan Shee, Newark, CA (US); Clarissa Lui, Menlo Park, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 477 days.

(21) Appl. No.: 17/171,951

(22) Filed: Feb. 9, 2021

(65) Prior Publication Data

US 2021/0269859 A1 Sep. 2, 2021

Related U.S. Application Data

(63) Continuation of application No. 15/159,399, filed on May 19, 2016, now Pat. No. 10,920,284, which is a continuation of application No. PCT/US2015/048533, filed on Sep. 4, 2015.

(60) Provisional application No. 62/046,135, filed on Sep. 4, 2014, provisional application No. 62/061,093, filed on Oct. 7, 2014.

(51) Int. Cl.
| C12Q 1/689 | (2018.01) |
| C12Q 1/04 | (2006.01) |
| G01N 33/53 | (2006.01) |
| G01N 33/569 | (2006.01) |

(52) U.S. Cl.
CPC ............... *C12Q 1/689* (2013.01); *C12Q 1/04* (2013.01); *G01N 33/53* (2013.01); *G01N 33/56911* (2013.01); *C12Q 2600/156* (2013.01); *C12Q 2600/158* (2013.01); *G01N 2469/10* (2013.01); *G01N 2469/20* (2013.01)

(58) Field of Classification Search
CPC .... C12Q 1/689; C12Q 1/04; C12Q 2600/156; C12Q 2600/158; G01N 33/53; G01N 33/56911; G01N 2469/10; G01N 2469/20
See application file for complete search history.

(56) References Cited

U.S. PATENT DOCUMENTS

| 4,683,195 A | 7/1987 | Mullis et al. |
| 5,340,747 A | 8/1994 | Eden et al. |
| 5,411,876 A | 5/1995 | Bloch et al. |
| 5,416,879 A | 5/1995 | Liu et al. |
| 5,456,652 A | 10/1995 | Eberle |
| 5,483,799 A | 1/1996 | Dalto |
| 6,254,826 B1 | 7/2001 | Acosta |
| 6,348,176 B1 | 2/2002 | Hammer et al. |
| 6,368,265 B1 | 4/2002 | Barkus et al. |
| 6,372,185 B1 | 4/2002 | Shumate et al. |
| 6,465,953 B1 | 10/2002 | Duggal |
| 6,468,474 B2 | 10/2002 | Bachand et al. |
| 6,509,193 B1 | 1/2003 | Tajima |
| 6,565,813 B1 | 5/2003 | Garyantes |
| 6,589,789 B1 | 7/2003 | Hubert et al. |
| 6,656,428 B1 | 12/2003 | Clark et al. |
| 6,689,615 B1 | 2/2004 | Murto et al. |
| 6,752,965 B2 | 6/2004 | Levy et al. |
| 6,797,518 B1 | 9/2004 | Jacobs et al. |
| 6,825,921 B1 | 11/2004 | Modlin et al. |
| 6,858,185 B1 | 2/2005 | Kopf-Sill et al. |
| 7,394,363 B1 | 7/2008 | Ghahramani |
| 7,544,324 B2 | 6/2009 | Tung et al. |
| 7,632,462 B2 | 12/2009 | Hoitllund et al. |
| 7,642,068 B2 | 1/2010 | Steiner et al. |
| 7,690,275 B1 | 4/2010 | Wiederin et al. |
| 8,008,066 B2 | 8/2011 | Lair et al. |
| 8,088,593 B2 | 1/2012 | Burd et al. |
| 8,211,386 B2 | 7/2012 | Talmer et al. |
| 8,218,091 B2 | 10/2012 | Rutter et al. |
| 8,309,035 B2 | 11/2012 | Chen et al. |
| 8,323,564 B2 | 12/2012 | Padmanabhan et al. |
| 8,383,421 B2 | 2/2013 | Yanagida et al. |
| 8,387,811 B2 | 3/2013 | Livingston et al. |
| 8,557,539 B2 | 10/2013 | Eden et al. |
| 8,894,946 B2 | 11/2014 | Nielsen et al. |
| 9,121,801 B2 | 9/2015 | Clark et al. |
| 9,168,523 B2 | 10/2015 | Ludowise et al. |
| 10,920,284 B2 | 2/2021 | Holmes et al. |
| 2002/0004019 A1 | 1/2002 | Bachand et al. |
| 2003/0180961 A1 | 9/2003 | Knezevic et al. |
| 2004/0248199 A1 | 12/2004 | Squirrell et al. |
| 2005/0026144 A1 | 2/2005 | Maes et al. |
| 2005/0059064 A1 | 3/2005 | Obst et al. |
| 2005/0095665 A1 | 5/2005 | Williams et al. |
| 2006/0257993 A1 | 11/2006 | McDevitt et al. |
| 2008/0176273 A1 | 7/2008 | Eden et al. |
| 2009/0019953 A1 | 1/2009 | Bommarito et al. |
| 2009/0030342 A1 | 1/2009 | Flanigan et al. |
| 2009/0306230 A1 | 12/2009 | Semikhodskii et al. |
| 2010/0077843 A1 | 4/2010 | Doraisamy et al. |
| 2010/0105074 A1 | 4/2010 | Covey et al. |
| 2010/0132487 A1 | 6/2010 | Haack et al. |
| 2010/0216155 A1 | 8/2010 | Hogan et al. |

(Continued)

FOREIGN PATENT DOCUMENTS

| EP | 1984520 A2 | 10/2008 |
| JP | H11142400 A | 5/1999 |

(Continued)

OTHER PUBLICATIONS

BOGAERTS P et al., Analytical validation of a novel high multiplexing real-time PCR array for the identification of key pathogens causative of bacterial ventilator-associated pneumonia and their associated resistance genes, Journal of Antimicrobial Chemotherapy, vol. 68, No. 2, Oct. 12, 2012, pp. 340-347.

(Continued)

*Primary Examiner* — Narayan K Bhat
(74) *Attorney, Agent, or Firm* — Sterne, Kessler, Goldstein & Fox P.L.L.C.

(57) ABSTRACT

Systems and methods for determining pathogens and antimicrobial resistance of pathogens in a sample are provided.

13 Claims, 12 Drawing Sheets

(56) References Cited

U.S. PATENT DOCUMENTS

| | | |
|---|---|---|
| 2013/0244241 A1 | 9/2013 | Fabra et al. |
| 2014/0170735 A1 | 6/2014 | Holmes et al. |
| 2017/0121759 A1 | 5/2017 | Jarvius et al. |

FOREIGN PATENT DOCUMENTS

| | | | | |
|---|---|---|---|---|
| JP | 2011069778 A | 4/2011 | | |
| WO | WO 90/08196 | * 7/1990 | ............... | C12Q 1/18 |
| WO | WO 1990008196 A1 | 7/1990 | | |
| WO | WO 2004061418 A2 | 7/2004 | | |
| WO | WO 2012025729 A1 | 3/2012 | | |
| WO | WO 2013052318 A1 | 4/2013 | | |
| WO | WO 2014100456 A1 | 6/2014 | | |
| WO | WO-2015189390 A1 | * 12/2015 | ............... | C12Q 1/04 |
| WO | WO 2015189390 A1 | 12/2015 | | |
| WO | WO 2016037051 A1 | 3/2016 | | |

OTHER PUBLICATIONS

Chen et al., Antimicrobial susceptibility testing using high surface-to-vol. ratio microchannels, Analytical Chemistry, Feb. 1, 2010, pp. 1012-1019.

International Search Report and Written Opinion dated Dec. 17, 15 for PCT/US2015/048533.

Pulido et al., Progress on the development of rapid methods for antimicrobial susceptibility testing, Journal of Antimicrobial Chemotherapy, vol. 68, No. 12, Jun. 30, 2013, pp. 2710-2717.

Tang et al., Rapid Antibiotic Susceptibility Testing in a Microfluidic pH Sensor, Analytical Chemistry, vol. 85, No. 5, Mar. 5, 2013, pp. 2787-2794.

* cited by examiner

PATHOGEN AND ANTIMICROBIAL RESISTANCE TESTING

RELATED APPLICATIONS

This application claims priority under 35 U.S.C. § 119(e) to U.S. Provisional Application No. 62/046,135, filed Sep. 4, 2014, and U.S. Provisional Application No. 62/061,093, filed Oct. 7, 2014, both of which are hereby incorporated by reference in their entireties.

BACKGROUND

Many human and animal diseases are caused by infection with a pathogen. While the growth of many pathogens can be slowed or stopped by antimicrobials, certain pathogens are resistant to one or more antimicrobials. Improvements are needed in systems and methods for the detection of pathogens and of antimicrobial resistance of pathogens.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Provided herein are embodiments for pathogen and pathogen antimicrobial resistance testing.

In embodiments, provided herein is a cartridge for analysis of a sample, comprising: an antimicrobial; a microorganism growth medium; and at least one reagent selected from a metabolic indicator, a reagent for a nucleic acid amplification reaction, and a reagent for a nucleic acid probe-based assay. Optionally, the cartridge further comprises a sample, which may comprise or may be suspected of comprising a pathogen. Optionally, the sample is a blood sample obtained from a subject, and the blood sample obtained from the subject may be about 500 µl or less. Optionally, the at least one reagent, the antimicrobial, and the microorganism growth medium are in separate fluidically isolated vessels in the cartridge. Optionally, the antimicrobial and the microorganism growth medium are in the same vessel in the cartridge. Optionally, the antimicrobial, the microorganism growth medium, and the at least one reagent are in the same vessel in the cartridge. Optionally, the antimicrobial is selected from an antibiotic, antiviral, antifungal, and antiparasitic. Optionally, the antimicrobial is an antibiotic. Optionally, the at least one reagent is a metabolic indicator. Optionally, the at least one reagent is a metabolic indicator and a reagent for a nucleic acid amplification reaction. Optionally, the at least one reagent is a metabolic indicator and a reagent for a nucleic acid probe-based assay. Optionally, the at least one reagent is a metabolic indicator, a reagent for a nucleic acid amplification reaction, and a reagent for a nucleic acid probe-based assay. Optionally, the metabolic indicator is selected from resazurin, 5-cyano-2,3-ditolyl tetrazolium choride (CTC), carboxyfluorescein diacetate succinimidyl ester (CFDA-SE), and luciferin. Optionally, the metabolic indicator is resazurin. Optionally, the reagent for a nucleic acid amplification reaction is a nucleic acid polymerase. Optionally, the reagent for a nucleic acid amplification reaction is a primer pair. Optionally, the primer pair is capable of specifically hybridizing to a nucleic acid, or a complement thereof, of a bacterial marker. Optionally, the bacterial marker is selected from 16S rRNA, 16s rDNA, 23 rRNA, rpoB, gyrB, dnaK, amoA, and mip. Optionally, the bacterial marker is 16S rRNA. Optionally, the primer pair is capable of specifically hybridizing to a nucleic acid, or a complement thereof, of an antimicrobial-resistance marker. Optionally, the reagent for a nucleic acid probe-based assay is a nucleic acid probe. Optionally, the nucleic acid probe is capable of specifically annealing to a nucleic acid, or a complement thereof, of a bacterial marker. Optionally, the bacterial marker is selected from 16S rRNA, 16s rDNA, 23 rRNA, rpoB, gyrB, dnaK, amoA, and mip. Optionally, the bacterial marker is 16S rRNA. Optionally, the nucleic acid probe is capable of specifically hybridizing to a nucleic acid, or a complement thereof, of an antimicrobial-resistance marker. Optionally, the cartridge may further comprise an antibody which binds to an antigen of a pathogen. Optionally, the cartridge further comprises a nucleic acid dye.

In embodiments, provided herein is a method for analysis of a sample, the method comprising: incubating at least a first portion of a sample comprising or suspected of comprising a pathogen with a microorganism growth medium, antimicrobial, and metabolic indicator to produce a reaction mixture, wherein the metabolic indicator is capable of being metabolized to produce a metabolic product; and detecting the metabolic product. Optionally, the sample is a blood sample obtained from a subject. Optionally, the blood sample obtained from the subject is about 500 µl or less. Optionally, the metabolic product generates a detectable signal. Optionally, the detectable signal is selected from fluorescence, color, and luminescence. Optionally, the metabolic indicator is selected from resazurin, 5-cyano-2,3-ditolyl tetrazolium choride (CTC), carboxyfluorescein diacetate succinimidyl ester (CFDA-SE), and luciferin. Optionally, the metabolic indicator is resazurin and the metabolic product is resorufin. Optionally, the antimicrobial is selected from an antibiotic, antiviral, antifungal, and antiparasitic. Optionally, the antimicrobial is an antibiotic. Optionally, the sample is incubated with the microorganism growth medium, anatimicrobial, and metabolic indicator for between about 1 hr to about 8 hrs. Optionally, the method further comprises pre-culturing the sample in the microorganism growth medium in the absence of the antimicrobial and metabolic indicator. Optionally, the method further comprises diluting the sample prior to incubating the sample. Optionally, the sample is diluted to about 1 to about $10^8$ pathogens/reaction mixture. Optionally, the method further comprises incubating at least a second portion of the sample or a second sample comprising or suspected of comprising a pathogen with at least one reagent selected from a reagent for a nucleic acid amplification reaction and a reagent for a nucleic acid probe-based assay. Optionally, the at least one reagent is a reagent for a nucleic acid amplification reaction and the method comprises incubating at least the second portion or a second sample under conditions sufficient to support the amplification of a nucleic acid of the pathogen in the sample and detecting amplification of the nucleic acid. Optionally, the at least one reagent is a reagent for a nucleic acid probe-based assay and the method comprises incubating at least the second portion or the second sample under conditions sufficient to support specifically hybridizing of a nucleic acid probe to a nucleic acid of the pathogen in the sample and detecting the nucleic acid of the pathogen. Optionally, the nucleic acid of the pathogen is a nucleic acid, or a complement thereof, of a bacterial marker. Optionally, the bacterial marker is selected from 16S rRNA, 16s rDNA, 23 rRNA, rpoB, gyrB, dnaK, amoA, and mip. Optionally, the bacterial marker is 16S rRNA. Optionally, the nucleic acid of the pathogen is a nucleic acid, or a complement thereof, of an antimicrobial-resistance marker. Optionally, the method further comprises receiving in a sample processing device a cartridge, wherein the sample processing device comprises a fluid handling system, and wherein the cartridge comprises the sample, the microorganism growth medium, the antimicrobial, and the metabolic indicator, and transferring by the fluid handling system the at least first portion of the sample into fluid communication with the microorganism growth medium, the antimicrobial, and the metabolic indicator.

In embodiments, provided herein is a method for analysis of a sample, the method comprising: receiving in a sample processing device a cartridge, wherein the sample processing device comprises a fluid handling system, and wherein the cartridge comprises: a sample comprising or is suspected of comprising a pathogen, a reagent for a nucleic acid amplification reaction, an antimicrobial, and a microorganism growth medium; transferring by the fluid handling system a first portion of the sample into fluid communication with the reagent for the nucleic acid amplification reaction, to generate a first mixture comprising the first portion of the sample and the reagent for the nucleic acid amplification reaction; transferring by the fluid handling system a second portion of the sample into fluid communication with the antimicrobial and the microorganism growth medium, to generate a second mixture comprising the second portion of the sample, the antimicrobial, and the microorganism growth medium; incubating the first mixture under conditions sufficient to support the amplification of a nucleic acid from the pathogen in the sample; culturing the second mixture under conditions sufficient to support growth of the pathogen in the second mixture; detecting amplification of the nucleic acid from the pathogen in the sample; and detecting growth of the pathogen in the sample. Optionally, detecting amplification of the nucleic acid from the pathogen in the sample comprises detecting fluorescence from a dye in the first mixture. Optionally, the detecting amplification of the nucleic acid from the pathogen in the sample and the detecting of the growth of the pathogen in the sample both occur no more than 24 hours after the cartridge is received in the sample processing device.

In embodiments, a method provided herein comprises receiving a sample processing device a cartridge, wherein the sample processing device comprises a fluid handling system, and wherein the cartridge comprises a sample comprising or is suspected of comprising a pathogen, an antimicrobial, a microorganism growth medium, and a nucleic acid probe capable of specifically hybridizing to a nucleic acid, or a complement thereof, of the pathogen, transferring by the fluid handling system a first portion of the sample into fluid communication with the nucleic acid probe, to generate a first mixture comprising the first portion of the sample and the nucleic acid probe; transferring by the fluid handling system a second portion of the sample into fluid communication with the antimicrobial and the microorganism growth medium, to generate a second mixture comprising the second portion of the sample, the antimicrobial, and the microorganism growth medium; incubating the first mixture under conditions sufficient to specifically hybridize to a nucleic acid, or a complement thereof, of the pathogen in the sample; culturing the second mixture under conditions sufficient to support growth of the pathogen; detecting the nucleic acid of the pathogen in the sample; and detecting growth of the pathogen in the sample.

In any embodiment, the sample is a blood sample obtained from a subject. In any embodiment, the blood sample obtained from the subject is about 500 µl or less. In any embodiment, the species of the pathogen is detected. In any embodiment, an antimicrobial resistance gene is detected. In any embodiment, the cartridge further comprises an antibody which binds to an antigen in a pathogen. In any embodiment, detecting growth of the pathogen in the sample comprises examining the second mixture with a cytometer. In any embodiment, examining comprises counting the number of pathogen cells. In any embodiment, examining comprises detecting an antigen of the pathogen. In any embodiment, examining comprises determining a ration or number of pathogen cells undergoing cell division. In any embodiment, detecting growth of the pathogen in the sample comprises examining the second mixture with a spectrophotometer. In any embodiment, examining comprises determining the optical density of the second mixture. In any embodiment, the cartridge further comprises a metabolic indicator, wherein the metabolic indicator is capable of being metabolized to produce a metabolic product, and the method comprises transferring by the fluid handling system the second portion of the sample into fluid communication with the antimicrobial, the microorganism growth medium, and the metabolic indicator to generate a second mixture comprising the second portion of the sample, the antimicrobial, the microorganism growth medium, and the metabolic indicator. In any embodiment, the growth of the pathogen is detected by detecting the metabolic product. In any embodiment, the metabolic product generates a detectable signal. In any embodiment, the detectable signal is selected from fluorescence, color, and luminescence. In any embodiment, the metabolic indicator is selected from resazurin, 5-cyano-2,3-ditolyl tetrazolium chloride (CTC), carboxyfluorescein diacetate succinimidyl ester (CFDA-SE), and luciferin. In any embodiment, the metabolic indicator is resazurin.

In embodiments, a system provided herein comprises an antimicrobial; a microorganism growth medium; at least one reagent selected from a metabolic indicator, a reagent for a nucleic acid amplification reaction, and a reagent for a nucleic acid probe-based assay; and a sample processing device, wherein the sample processing device comprises a fluid handling system and at least one detector. Optionally, the system further comprises a cartridge, wherein the cartridge comprises the antimicrobial, microorganism growth medium, and the at least one reagent. Optionally, the antimicrobial, microorganism growth medium, and the at least one reagent are in separate fluidically isolated vessels in the cartridge. Optionally, the antimicrobial and microorganism growth medium are in the same vessel in the cartridge. Optionally, the antimicrobial, microorganism growth medium, and the at least one reagent are in the same vessel in the cartridge. Optionally, the cartridge further comprises a sample comprising or suspected of comprising a pathogen. Optionally, the sample is a blood sample obtained from a subject. Optionally, the blood sample obtained from the subject is about 500 µl or less. Optionally, the at least one reagent is a metabolic indicator. Optionally, the at least one reagent is a metabolic indicator and a reagent for a nucleic acid amplification reaction. Optionally, the at least one reagent is a metabolic indicator and a reagent for a nucleic acid probe-based assay. Optionally, the at least one reagent is a metabolic indicator, a reagent for a nucleic acid amplification reaction, and a reagent for a nucleic acid probe-based assay. Optionally, the metabolic indicator is selected from resazurin, 5-cyano-2,3-ditolyl tetrazolium chloride (CTC), carboxyfluorescein diacetate succinimidyl ester (CFDA-SE), and luciferin. Optionally, the metabolic indicator is resazurin. Optionally, the reagent for a nucleic acid amplification is a nucleic acid polymerase. Optionally, the reagent for a nucleic acid amplification reaction is a primer pair. Optionally, the primer pair is capable of specifically hybridizing to a nucleic acid, or a complement thereof, of a bacterial marker. Optionally, the bacterial marker is selected from 16S rRNA, 16S rDNA, 23 rRNA, rpoB, gyrB, dnaK, amoA, and mip. Optionally, the bacterial marker is 16S rRNA. Optionally, the primer pair is capable of specifically hybridizing to a nucleic acid, or a complement thereof, of an antimicrobial-resistance marker. Optionally, the reagent for a nucleic acid probe-based assay is a nucleic acid probe. Optionally, the nucleic acid probe is capable of specifically hybridizing to a nucleic acid, or a complement thereof, of a bacterial marker. Optionally, the bacterial marker is selected from 16S rRNA, 16S rDNA, 23 rRNA, rpoB, gyrB, dnaK, amoA, and mip. Optionally, the bacterial marker is 16S rRNA. Optionally, the nucleic acid probe is capable of specifically hybridizing to a nucleic acid, or a complement thereof, of an antimicrobial-resistance marker. Optionally, the cartridge further comprises an antibody which binds to an antigen of a pathogen. Optionally, the cartridge further comprises a nucleic acid dye. Optionally, the at least one detector is selected from a spectrophotometer, photomultiplier, photodiode, camera, and a cytometer.

In embodiments, a method provided herein comprises determining the species, sub-species, or strain of a pathogen in a sample.

In embodiments, a method provided herein comprises identifying an antimicrobial resistance gene or mutation in a pathogen or sample.

In embodiments, a method provided herein comprises detecting growth of a pathogen, wherein detecting growth comprises examining a culture with a cytometer.

In embodiments, examining a culture for growth with a cytometer comprises counting a number of pathogen cells, detecting an antigen in pathogen cells, detecting DNA content of pathogen cells, or obtaining a measurement of pathogen cells undergoing cell division.

In embodiments, a method provided herein comprises detecting growth of a pathogen, wherein detecting growth comprises examining a culture with a spectrophotometer. Optionally, the optical density of the culture may be determined.

In embodiments, in a method provided herein for detecting amplification of a nucleic acid of a pathogen in a sample and for detecting of the growth of a pathogen in a sample, both occur no more than 24, 16, 12, 10, 8, 6, 5, 4, 3, 2, or 1 hours after a cartridge containing a sample containing the pathogen is received in the sample processing device.

Any reference to or description of a "sample" herein also applies to a portion of a sample, unless the context clearly dictates otherwise.

In embodiments, any of the processes described herein may be performed by automated steps performed by one or more components (e.g. fluid handling system, cytometer, etc.) within a sample processing device. The components may be controlled by a controller which may execute sample processing protocols.

Other goals and advantages of the invention will be further appreciated and understood when considered in conjunction with the following description and accompanying drawings. While the following description may contain specific details describing particular embodiments of the invention, these should not be construed as limitations to the scope of the invention but rather as exemplifications of possible embodiments. For each aspect of the invention, many changes and modifications can be made within the scope of the invention without departing from the spirit thereof.

Figure 1:
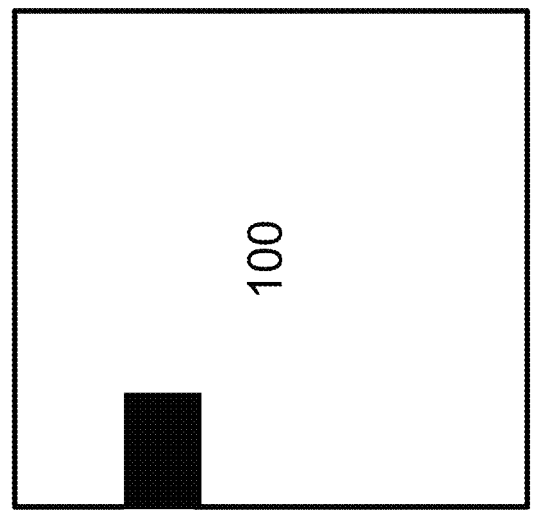
FIG. 1 shows an exemplary schematic of a sample and sample processing device provided herein.
Figure 1:
Figure 1:

It is noted that the drawings and elements therein are not necessarily drawn to shape or scale. For example, the shape or scale of elements of the drawings may be simplified or modified for ease or clarity of presentation. It should further be understood that the drawings and elements therein are for exemplary illustrative purposes only, and not be construed as limiting in any way.

DETAILED DESCRIPTION

Provided herein are embodiments for identifying pathogens and identifying antimicrobial resistance of pathogens. Various features described herein may be applied to any of the particular embodiments set forth below or for any other types of embodiments for or involving the identification of pathogens or antimicrobial resistance of pathogens. Systems and methods described herein may be applied as a stand-alone system or method, or as part of an integrated system or method. It shall be understood that different aspects of the disclosed systems and methods can be appreciated individually, collectively, or in combination with each other.

Sample

A sample as used herein may be any material which may contain or is suspected of containing one or more pathogens. A sample may be, for example, a bodily fluid, a secretion, or a tissue sample. Examples of samples may include but are not limited to, blood, serum, saliva, urine, gastric and digestive fluid, tears, stool, semen, vaginal fluid, interstitial fluids derived from tumorous tissue, ocular fluids, sweat, mucus, earwax, oil, glandular secretions, breath, spinal fluid, hair, fingernails, skin cells, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, microbiota, meconium, breast milk or other excretions. A sample may be provided from, for example, a human, animal, plant, microorganism, the environment, food, or from other sources. In embodiments, a sample may contain material obtained from a swab from a subject (e.g. a nasal swab). As used herein, a sample refers to an entire original sample or any portion thereof.

In embodiments, a sample may be obtained from various locations on a subject (e.g. arm, ear, hand, foot, etc.). In embodiments, a sample may be obtained from a subject's finger or toe. As used herein, a subject refers to a vertebrate, and includes a mammal and human. Mammals include, but are not limited to, murines, simians, humans, farm animals, sport animals, and pets.

The methods provided herein are capable of detecting the pathogen from a small volume or amount of a sample obtained from a subject. In embodiments, a sample collected from a subject may have a volume of about or less than 1000, 900, 800, 700, 600, 500, 400, 300, 200, 100, 90, 80, 70, 60, 50, 40, 30, 25, 20, 15, 10, or 5 microliters. In an embodiment, the bodily fluid sample obtained from the subject is a whole blood sample. In a particular embodiment, the whole blood sample is obtained by a fingerstick and has a volume of about or less than 1000, 900, 800, 700, 600, 500, 400, 300, 200, 100, 90, 80, 70, 60, 50, 40, 30, 25, 20, 15, 10, or 5 microliters. For example, in embodiments, a sample collected from a subject may be blood which is collected from the subject's finger and which has a volume of about 500 microliters or less. In another embodiment, a sample may be obtained by contacting a swab (eg. nasal swab) or a solid sample such as feces or a tissue sample with a buffer or other liquid solution that is about or less than 1000, 900, 800, 700, 600, 500, 400, 300, 200, 100, 90, 80, 70, 60, 50, 40, 30, 25, 20, 15, 10, or 5 microliters.

Where the pathogen may be present in low copy numbers, such as at an early stage in the infection, a large volume or amount of sample and/or a long culture period is typically required in order to increase the copy numbers to a detectable level. In contrast, the methods provided herein allow for detection of the pathogen in a small volume/amount of sample and in a shorter period of time, even for samples that contain low copy numbers of the pathogen.

Pathogens and Antimicrobials

The sample may be tested to determine whether a particular pathogen is present in the sample and/or to determine whether a pathogen in the sample is resistant or susceptible to an antimicrobial, including but not limited to, an antibiotic, antiviral, antifungal, and antiparasitic. As used herein, pathogens refer to microorganisms which may cause disease in multi-cell organisms such as humans, animals, or plants, and may include, for example, bacteria, fungi, protists, parasites, and viruses.

Bacteria include those that cause diseases such as diphtheria (e.g., *Corynebacterium diphtheria*), pertussis (e.g., *Bordetella pertussis*), anthrax (e.g., *Bacillus anthracia*), typhoid, plague, shigellosis (e.g., *Shigella dysenteriae*), botulism (e.g., *Clostridium botulinum*), tetanus (e.g., *Clostridium tetani*), tuberculosis (e.g., *Mycobacterium tuberculosis*), bacterial pneumonias (e.g., *Haemophilus influenzae*), cholera (e.g., *Vibrio cholerae*), salmonellosis (e.g., *Salmonella typhi*), peptic ulcers (e.g., *Helicobacter pylori*), Legionnaire's Disease (e.g. *Legionella* spp.), and Lyme disease (e.g. *Borrelia burgdorferi*). Other pathogenic bacteria include *Escherichia coli, Clostridium perfringens, Clostridium difficile, Pseudomonas aeruginosa, Staphylococcus aureus*, and *Streptococcus pyogenes*. Further examples of bacteria include *Staphylococcus epidermidis, Staphylococcus* sp., *Streptococcus pneumoniae, Streptococcus agalactiae, Enterococcus* sp., *Bacillus cereus, Bifidobacterium bifidum, Lactobacillus* sp., *Listeria monocytogenes, Nocardia* sp., *Rhodococcus equi, Erysipelothrix rhusiopathiae, Propionibacterium acnes, Actinomyces* sp., *Mobiluncus* sp., *Peptostreptococcus* sp., *Neisseria gonorrhoeae, Neisseria meningitides, Moraxella catarrhalis, Veillonella* sp., *Actinobacillus actinomycetemcomitans, Acinetobacter baumannii, Brucella* sp., *Campylobacter* sp., *Capnocytophaga* sp., *Cardiobacterium hominis, Eikenella corrodens, Francisella tularensis, Haemophilus ducreyi, Helicobacter pylori, Kingella kingae, Legionella pneumophila, Pasteurella multocida, Klebsiella granulomatis*, Enterobacteriaceae, *Citrobacter* sp., *Enterobacter* sp., *Klebsiella pneumoniae, Proteus* sp., *Salmonella enteriditis, Shigella* sp., *Serratia marcescens, Yersinia enterocolitica, Yersinia pestis, Aeromonas* sp., *Plesiomonas shigelloides, Vibrio cholerae, Vibrio parahaemolyticus, Vibrio vulnificus, Acinetobacter* sp., *Flavobacterium* sp., *Burkholderia cepacia, Burkholderia pseudomallei, Xanthomonas maltophilia, Stenotrophomonas maltophila, Bacteroides Bacteroides* sp., *Prevotella* sp., *Fusobacterium* sp., and Spirillum minus. Antibiotics are agents used to kill, inhibit, or slow the growth of bacteria or other microorganisms and include, but are not limited to, aminoglycosides (such as amikacin, gentamicin, kanamycin, neomycin, netilmicin, tobramycin, paromomycin, streptomycin, and spectinomycin), ansamycins (such as geldanamycin, herbimycin, and rifaximin), carbacephem (such as loracarbef) carbapenems (such as ertapenem, doripenem, imipenem/cilastatin, and meropenem), cephalosporins (such as cefadroxil, cefazolin, cefalotin (cefalothin), cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil and ceftobiprole), glycopeptides (such as teicoplanin, vancomycin, telavancin, dalbavancin, and oritavancin), lincosamides (such as clindamycin and lincomycin), lipopetides (such as daptomycin), macrolides (such as azithromycin, clarithromycin, dirithromycin, erythromycin, roxithromycin, troleandomycin, telithromycin, and spiramycin), monobactams (such as aztreonam), nitrofurans (such as furazolidone, and nitrofurantoin), oxazolidinones (such as linezolid, posizolid, radezolid, and torezolid), penicillins (such as amoxicillin, ampicillin, azlocillin, carbenicillin, cloxacillin, dicloxacillin, flucloxacillin, mexlocillin, methicillin, nafcillin, oxacillin, penicillin G, penicillin V, piperacillin, temocillin, and ticarcillin), polypeptides (such as bacitracin, colistin, and polymyxin B), quinolones/fluoroquinolones (such as ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, and temafloxacin), sulfonamides (such as mafenide, sulfacetamide, sulfadiazine, silver sulfadiazine, sulfadimethoxine, sulfamethizole, sulfamethoxazole, sulfanilamide, sulfasalazine, sulfisoxazole, trimethoprim-sulfamethoxazole, and sulfonamidochrysoidine), tetracylines (such as demeclocycline, doxycycline, minocycline, oxytetracycline, and tetracycline), antimycobacteria (such as clofazimine, dapsone, capreomycin, cycloserine, ethambutol, ethionamide, isoniazid, pyrazinamide, rifampicin, rifabutin, rifapentine, streptomycin), arsphenamine, chloramphenicol, fosfomycin, fusidic acid, metronidazole, mupirocin, platensimycin, quinupristin/dalfopristin, thiamphenicol, tigecycline, tinidazole, trimethoprim, and teixobactin.

Viruses include, but are not limited to, measles, mumps, rubella, poliomyelitis, hepatitis (e.g. hepatitis A, B, C, delta, and E viruses), influenza, adenovirus, rabies, yellow fever, Epstein-Barr virus, herpesviruses, papillomavirus, Ebola virus, influenza virus, Japanese encephalitis, dengue virus, hantavirus, Sendai virus, respiratory syncytial virus, othromyxoviruses, vesicular stomatitis virus, visna virus, cytomegalovirus, and human immunodeficiency virus (HIV). Antivirals are agents used to kill, inhibit, or slow the growth of viruses and include, but are not limited to, anti-(HIV) agents (such as abacavir, didanosine, emtricitabine, lamivudine, stavudine, tenofovir disoproxil fumarate, zidovudine, delavirdine, efavirenz, etravirine, nevirapine, rilpivirine, atazanavir, darunavir, fosamprenavir, indinavir, nelfinavir, ritonavir, saquinavir, tipranavir, enfuvirtide, maraviroc, dolutegravir, elvitegravir, raltegravir, cobicistat, and combinations thereof), anti-influenza virus agents (such as zanamivir, oseltamivir phosphate, peramivir, amantadine, and rimantadine), anti-herpes virus agents (such as acyclovir, valacyclovir, penciclovir, idoxuridine, vidarabine, trifluridine, foscarnet and famciclovir), anti-hepatitis virus agents (such as adefovir, lamivudine, telbivudine, tenofovir, famciclovir, entecavir, ribavirin, telaprevir, simeprevir, sofosbuvir, ledipasvir, ombitasvir, paritaprevir, ritonavir, dasabuvir, and boceprevir), anti-cytomegalovirus (CMV) agents (such as ganciclovir, cidofovir, valganciclovir, foscarnet, maribavir, and leflunomide), anti-respiratory syncytial virus (RSV) agents (such as ribavirin and palivizumab), and anti-varicella-zoster virus (VSV) agents (such as acyclovir, valacyclovir, penciclovir, famciclovir, brivudin, foscarnet, and vidarabine).

Fungi include, but are not limited to, *Acremoniuin* spp., *Aspergillus* spp., *Epidermophytoni* spp., *Exophiala jeanselmei*, *Exserohilunm* spp., *Fonsecaea compacta*, *Fonsecaea pedrosoi*, *Fusarium oxysporum*, *Basidiobolus* spp., *Bipolaris* spp., *Blastomyces derinatidis*, *Candida* spp., *Cladophialophora carrionii*, *Coccoidiodes immitis*, *Conidiobolus* spp., *Cryptococcus* spp., *Curvularia* spp., *Fusarium solani*, *Geotrichum candidum*, *Histoplasma capsulatum* var. *capsulatum*, *Histoplasma capsulatum* var. *duboisii*, *Hortaea werneckii*, *Lacazia loboi*, *Lasiodiplodia theobromas*, *Leptosphaeria senegalenisis*, *Piedra iahortae*, *Pityriasis versicolor*, *Pseudallesheria boydii*, *Pyrenochaeta romeroi*, *Rhizopus arrhizus*, *Scopulariopsis brevicaulis*, *Scytalidium dimidiatum*, *Sporothrix schenckii*, *Trichophyton* spp., *Trichosporon* spp., *Zygomycete* fungi, *Madurella grisea*, *Madurella mycetomatis*, *Malassezia furfur*, *Microsporum* spp., *Neotestudina rosatii*, *Onychocola canadensis*, *Paracoccidioides brasiliensis*, *Phialophora verrucosa*, *Piedraia hortae*, *Absidia coryinbifera*, *Rhizomucor pusillus*, and *Rhizopus arrhizus*. Antifungals are agents used to kill, inhibit, or slow the growth of fungi and include, but are not limited to, polyene antifungals (such as amphotericin B, candicin, filipin, hamycin, natamycin, nystatin, and rimocidin), azole antifungals (such as abafungin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, efinaconazole, epoxiconazole, fluconazole, isavuconazole, itraconazole, posaconazole, propiconazole, ravuconazole, and terconazole, voriconazole), and echinocandins (such as anidulafungin, caspofungin, and micofungin).

Parasites include, but are not limited to, protozoa, nematodes, cestodes, trematodes, and other parasites, such as those responsible for diseases, including, but not limited to, malaria (e.g. *Plasmodium falciparum*), hookworm, tapeworms, helminths, whipworms, ringworms, roundworms, pinworms, ascarids, filarids, onchocerciasis (e.g., *Onchocerca volvulus*), schistosomiasis (e.g. *Schistosoma* spp.), toxoplasmosis (e.g. *Toxoplasma* spp.), trypanosomiasis (e.g. *Trypanosoma* spp.), leishmaniasis (*Leishmania* spp.), giardiasis (e.g. *Giardia lamblia*), amoebiasis (e.g. *Entamoeba histolytica*), filariasis (e.g. *Brugia malayi*), and trichinosis (e.g. *Trichinella spiralis*). Antiparasitics are agents used to kill, inhibit, or slow the growth of parasites and include, but are not limited to, antinematodes (such as mebendazole, pyrantel pamoate, thiabendazole, diethylcarbamazine, and ivermectin), anticestodes (such as niclosamide, praziquantel, and albendazole), antitrematodes (such as praziquantel), antiamoebics (such as rifampin and amphotericin B), and antiprotozoals (such as melarsoprol, eflornithine, metronidazole, tinidazole, and miltefosine).

Sample Preparation

After a sample is collected, it may undergo one or more sample preparation steps before being assayed. Alternatively, after a sample is collected, it may be directly assayed. In an embodiment, multiple samples may be obtained from a subject and each sample tested separately for a pathogen. For example, a first sample, or at least a portion of the first sample, may be tested to determine whether a pathogen is present in the sample and a second sample, or at least a portion of the second sample, may be tested to determine whether a pathogen in the sample is resistant or susceptible to an antimicrobial. In another embodiment, a single sample may be divided into at least two fluidically isolated portions (e.g. at least a first portion and a second portion). In certain embodiments, each portion of a sample may be directly used to test for a pathogen. The first portion may be used for at least a first laboratory test or part thereof, and the second portion may be used for at least a second laboratory test or part thereof. In embodiments, a first portion of a sample may be used in a first laboratory test to determine whether a particular pathogen of interest is present in the sample, and a second portion of the sample may be used in a second laboratory test may be to determine whether a pathogen in a sample is resistant or susceptible to an antimicrobial.

In other embodiments, a pathogen in a sample may first be enriched or concentrated (e.g. by physical methods, such as use of an antibody-based capture surface for the pathogen, culturing the pathogen, centrifugation to move pathogens towards the bottom of a tube containing a liquid suspension of the pathogen, or filtration to capture the pathogens from a liquid suspension of the pathogen). The enriched or concentrated sample may be directly tested for the pathogen. Alternatively, the enriched or concentrated sample may be divided into at least two fluidically isolated portions and each portion tested for the pathogen. As described above, the first portion may be used for at least a first laboratory test or part thereof, and the second portion may be used for at least a second laboratory test or part thereof. In embodiments, a first portion of a sample may be used in a first laboratory test to determine whether a particular pathogen of interest is present in the sample, and a second portion of the sample may be used in a second laboratory test may be to determine whether a pathogen in a sample is resistant or susceptible to an antimicrobial.

In a particular embodiment, the sample is pre-cultured in a microorganism growth medium prior to testing for a pathogen. A "microorganism growth medium" or "growth medium" may be used interchangeably and may be any suitable nutrient base which is sufficient to support the growth of a pathogen of interest. A microorganism growth media may be liquid, semi-solid, or solid. The sample may be pre-cultured for about 15, 14, 13, 12, 11, 10, 9, 8, 7, 6, 5, 4, 3, 2, or 1 hrs, or less. In an embodiment, the sample is pre-cultured for about 1 to about 8 hrs. In another embodiment, the sample is pre-cultured for about 2 to about 7 hrs. In yet another embodiment, the sample is pre-cultured for about 3 to about 6 hrs, about 3 to about 5 hrs, or about 3 to about 4 hrs. In a further embodiment, the sample is pre-cultured for about 2 to 3 hours, about 2 to about 4 hrs, about 2 to about 5 hrs, or about 2 to about 6 hrs. In another embodiment, the sample is cultured for about 1 to about 2 hrs, about 1 to about 3 hrs, about 1 to about 4 hours, about 1 to about 5 hours, or about 1 to about 6 hrs.

In an embodiment, the sample is pre-cultured until the pathogen is grown to mid-log phase. In another embodiment, the sample is pre-cultured until the pathogen is grown to a concentration of about $10^{10}$ pathogens/ml, about $10^9$ pathogens/ml, about $10^8$ pathogens/ml, about $10^7$ pathogens/ml, about $10^6$ pathogens/ml, about $10^5$ pathogens/ml, about $10^4$ pathogens/ml, about $10^3$ pathogens/ml, or about $10^2$ pathogens/ml, or greater. In an embodiment, the sample is pre-cultured until the pathogens are grown to a concentration of about $10^9$ to about $10^6$ pathogens/ml, about $10^9$ to about $10^7$ pathogens/ml, or about $10^9$ to about $10^8$ pathogens/ml. In yet another embodiment, the pathogens are grown to a concentration of about $10^8$ to about $10^6$ pathogens/ml, or about $10^8$ to about $10^7$ pathogens/ml.

The pre-cultured sample may then be tested for a pathogen or divided into at least two fluidically isolated portions to test for the pathogen.

In another embodiment, the pre-cultured sample or a sample without pre-culture may be diluted prior to testing for a pathogen to obtain one or more test reaction mixtures having a concentration of about 1 to about $10^8$ pathogens/reaction, $10^1$ to about $10^8$ pathogens/reaction, about $10^2$ to about $10^8$ pathogens/reaction, about $10^3$ to about $10^8$ pathogens/reaction, about $10^4$ to about $10^8$ pathogens/reaction, about $10^5$ to about $10^8$ pathogens/reaction, about $10^6$ to about $10^8$ pathogens/reaction, or about $10^7$ to about $10^8$ pathogens/reaction. In another embodiment, the sample is diluted to a concentration of about $10^1$ to about $10^7$ pathogens/reaction, about $10^1$ to about $10^6$ pathogens/reaction, about $10^1$ to about $10^5$ pathogens/reaction, about $10^1$ to about $10^4$ pathogens/reaction, about $10^1$ to about $10^3$ pathogens/reaction, or about $10^1$ to about $10^2$ pathogens/reaction. In an embodiment, the sample is diluted to a concentration of about 1, $10^1$, $10^2$, $10^3$, $10^4$, $10^5$, $10^6$, $10^7$, or $10^8$ pathogens/reaction, or any range in between.

Other sample preparation steps may include one or more of the following, depending on the type of assay to be performed: slicing, mincing, or dividing a tissue sample into two or more pieces; mixing, stirring, lysing, sonicating, homogenizing, fixing, or performing any other treatment of a sample or of a portion of the sample; centrifuging of a sample or a portion thereof; filtering (e.g., passing the sample or a portion thereof through a filter or membrane); allowing or causing a blood sample to coagulate; concentrating the sample, or of a portion of the sample (e.g., by sedimentation or centrifugation of a blood sample, or of a solution containing a homogenate of tissue from a tissue sample, or with electromagnetic beads) to provide a pellet and a supernatant; dyeing the sample or a portion of the sample with a dye; adding markers or reagents to the sample; or otherwise preparing for detection, visualization, or quantification of the sample, a portion of a sample, a component part of a sample, or a portion of a cell or structure within a sample.

Methods for Detecting Pathogens

Various methods may be used to determine whether a particular pathogen is present in a sample. For example, a sample may be used in an immunoassay to assay for an antigen (typically a polypeptide) which is present in a pathogen of interest. Alternatively, an immunoassay may involve using an antigen to detect the presence of an antibody in the sample generated against a pathogen. Immunoassays include, for example, ELISAs, immunoblotting, and antibody-based cell-staining for microscopy.

For example, an ELISA generally involves at least one antibody capable of specifically binding an antigen of interest (e.g., an antigen that is indicative of influenza viral infection). A sample containing or suspected to contain the antigen of interest is immobilized on a support (e.g., microarrays, microbeads, tips, sample transfer devices, cuvettes, capillaries or other tubes, reaction chambers, or any other suitable support having a surface for immobilization) either non-specifically (e.g., via adsorption to the surface) or specifically (e.g., via capture by another antibody specific to the same antigen, in a "sandwich" ELISA). After the antigen is immobilized, the detection antibody is added, forming a complex with the antigen. The detection antibody can be conjugated to an enzyme, or can itself be detected by a secondary antibody which is in turn conjugated to an enzyme. Upon addition of a substrate for the conjugated enzyme, a detectable signal is generated which indicates the presence and/or quantity of the antigen in the sample. The choice of substrates will depend on the enzyme conjugated. Suitable substrates include fluorogenic and chromogenic substrates.

In some ELISAs, a solid phase capture surface can include an attached first antibody to which a sample (e.g., diluted blood, plasma, or other sample) can be added. If present, an antigen in the sample can bind to the first antibody and become immobilized. An enzyme reagent can be added that includes, for example, an antibody coupled or conjugated to an enzyme (e.g., alkaline phosphatase or horseradish peroxidase) that produces a detectable product, or can be otherwise detected. If the antibody portion of the enzyme reagent can bind the antigen, then the enzyme reagent also becomes immobilized at the capture surface. Addition of a substrate for the enzyme can result in a product producing an effect, for example, light that can be measured and plotted. In this manner the amount of antigen present in a sample can be measured.

In another example, a sample may be used in a nucleic acid amplification-based test to assay for a nucleic acid sequence which is present in a pathogen of interest. Nucleic acid amplification reactions which may be used include amplification methods which involve thermocycling (e.g.

polymerase chain reaction (PCR)) and isothermal amplification methods (e.g. strand displacement amplification (SDA), rolling circle amplification (RCA), loop-mediated isothermal amplification (LAMP), helicase-dependent amplification (HDA), and the amplification methods described in WO 2014/145291, WO 2014/145296, and WO 2014/145298, the content of each of which is herein incorporated by reference in its entirety for all purposes). Exemplary methods for RNA amplification include in vitro transcription. In reverse transcription PCR (RT-PCR), RNA is first reverse transcribed into cDNA, followed by its exponential amplification in a PCR reaction. The two most commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers. The derived cDNA can then be used as a template in the subsequent PCR reaction.

Typically, nucleic acid amplification reactions to assay for a pathogen of interest will use at least one, and more commonly, at least two polynucleotide primers (i.e. primer pair) which specifically hybridize to a nucleic acid or complement thereof, of the pathogen of interest, and which serve as the initiation points for the generation of copies of the respective nucleic acid. Conditions sufficient to support amplification of a nucleic acid are known in the art, and are described in, for example, WO 2014/145291, WO 2014/145296, and WO 2014/145298. For example, conditions for PCR typically involve 1) a denaturation step during which a reaction mixture comprising a sample comprising a target DNA, a primer pair, Taq polymerase, and deoxynucleoside triphosphates (dNTPs), is heated to 94-96° C. for about 1-10 min to denature double-stranded DNA to single stranded DNA; 2) an annealing step during which the reaction temperature is lowered to about 50-65° C. for about 20-40 seconds to allow the primers to anneal to the single-stranded DNA template; and 3) an extension/elongation step during which the reaction temperature is adjusted to allow synthesis of a new DNA strand complementary to the DNA template strand by adding dNTPs that are complementary to the template in the 5' to 3' direction. The extension/elongation temperature may vary depending on the DNA polymerase used. For example, when using Taq polymerase, the extension/elongation temperature is typically 72° C. The above three steps may be repeated, typically 20-40 times, called cycles, until the nucleic acid is sufficiently amplified.

Nucleic acid amplification assays may be measured by monitoring the increase in fluorescence of the reaction (for example, in assays in which a fluorescent dye which intercalates with double-stranded DNA is used) or by monitoring the increase in absorbance or turbidity of the reaction (for example, in assays in which the pyrophosphate that is generated, as a result of nucleotide incorporation during DNA synthesis, reacts with Mg++ to form insoluble magnesium pyrophosphate). Nucleic acid amplification assays may be further analyzed, for example, by obtaining fluorescence, absorbance, or turbidity values over a period of time, and analyzing the data to identify an inflection point indicating the presence or amount of a nucleic acid of interest in a sample. This analysis maybe performed, for example, by fitting the data to an exponential curve and selecting the inflection point based on a threshold value above baseline.

In yet another example, the pathogen may be detected in a nucleic acid probe-based assay. These nucleic acid probe-based assays may contain one or more nucleic acid probes which specifically hybridize with a nucleic acid, or its complement, of a pathogen. The target nucleic acid may be, for example, DNA, RNA, mRNA, miRNA, rRNA, or tRNA. The nucleic acid probe of this invention may comprise DNA, RNA, modified nucleotides (e.g. methylated or labeled nucleotides), modified backbone chemistries (e.g. morpholine ring-containing backbones), nucleotide analogs, or combinations of two or more of these. The probe can be the coding or complementary strand of a complete gene or gene fragment, or an expression product thereof. The nucleotide sequence of the probe can be any sequence having sufficient complementarity to a nucleic acid sequence in a sample to allow for hybridization of the probe to the target nucleic acid in the sample under a desired hybridization condition. Ideally, the probe will hybridize only to the nucleic acid target of interest in the sample and will not bind non-specifically to other non-complementary nucleic acids in the sample or other regions of the target nucleic acid in the sample. In embodiments, the target nucleic acid may be a nucleic acid that has been amplified by, for example, PCR, such that the nucleic acid probe is used to detect the amplified nucleic acid.

The hybridization conditions can be varied according to the degree of stringency desired in the hybridization reaction. For example, if the hybridization conditions are for high stringency, the probe will bind only to the nucleic acid sequences in the sample with which it has a very high degree of complementarity. Low stringency hybridization conditions will allow for hybridization of the probe to nucleic acid sequences in the sample which have some complementarity but which are not as highly complementary to the probe sequence as would be required for hybridization to occur at high stringency. The hybridization conditions will vary depending on the biological sample, probe type and target. An artisan will know how to optimize hybridization conditions for a particular application of the present method, or alternatively, how to design nucleic acid probes for optimal use under a specified set of conditions. Hybridization conditions for primers used in nucleic acid amplification reactions may similarly be optimized.

The nucleic acid probe may be linked to a label, for example, a hapten, biotin, digoxigenin, fluorescein isothiocyanate (FITC), dinitrophenyl, amino methyl coumarin acetic acid, acetylaminofluorene and mercury-sulfhydryl-ligand complexes, chromogenic dyes, fluorescent dyes, and any other suitable label for detection of the target nucleic acid. In some embodiments, multiple probes, each having a different target nucleic acid and a different label, are hybridized to a single sample simultaneously, such as about or more than about 1, 2, 3, 4, 5, 6, 7, 8, 9, 10, 11, 12, 13, 14, 15, 16, 17, 18, 19, 20, or more different probes.

In some embodiments, a nucleic acid probe which contains a nucleotide sequence complementary to a portion of a nucleic acid template strand (or strand having a similar or identical sequence) and which contains one or both of a fluorescent reporter (fluorophore) and a quencher are included in a reaction provided herein. In an example, a nucleic acid probe may contain a fluorescent reporter at its 5' or 3' terminus, and a quencher at the other terminus. In another example, a nucleic acid probe may contain a fluorescent reporter at its 5' or 3' terminus, and it may be annealed to a nucleic acid primer containing a quencher. The nucleic acid primer containing a quencher may contain the quencher at a position in the primer such that when the nucleic acid probe is annealed to the primer, the fluorescent reporter is quenched. In probes containing a fluorescent reporter and quencher pair, the fluorescent reporter and quencher may be selected so that the quencher can effectively quench the reporter. In some embodiments, a fluorescent reporter is paired with a quencher where the emission maximum of the fluorescent reporter is similar to the absorption maximum of the quencher.

Fluorophores that may be used as the fluorescent reporter include, for example, CAL Fluor Gold, CAL Fluor Orange, Quasar 570, CAL Fluor Red 590, CAL Fluor Red 610, CAL Fluor Red 610, CAL Fluor Red 635, Quasar 670 (Biosearch Technologies), VIC, NED (Life Technologies), Cy3, Cy5, Cy5.5 (GE Healthcare Life Sciences), Oyster 556, Oyster 645 (Integrated DMA Technologies), LC red 610, LC red 610, LC red 640, LC red 670, LC red 705 (Roche Applies Science), Texas red, FAM, TET, HEX, JOE, TMR, and ROX. Quenchers that may be used include, for example, DDQ-I, DDQ-II (Eurogentee), Eclipse (Epoch Biosciences), Iowa Black FQ, Iowa Black RQ (Integrated DNA Technologies), BHQ-1, BHQ-2, BHQ-3 (Biosearch Technologies), QSY-7, QSY-21 (Molecular Probes), and Dabcyl.

In one embodiment, nucleic acid probes are covalently or non-covalently coupled to a substrate. Non-limiting examples of substrates to which nucleic acid probes may be coupled include microarrays, microbeads, pipette tips, sample transfer devices, cuvettes, capillaries or other tubes, reaction chambers, or any other suitable format. For example, microbeads useful in coupling nucleic acid probes are known in the art, and include magnetic and non-magnetic beads. Microbeads can be labeled with 1, 2, 3, 4, 5, 6, 7, 8, 9, 10, or more dyes to facilitate coding of the beads and identification of nucleic acid probes joined thereto. Coding of microbeads can be used to distinguish at least 10, 50, 100, 200, 300, 400, 500, 600, 700, 800, 900, 1000, 1500, 2000, 5000, or more different microbeads in a single assay, each microbead corresponding to a different nucleic acid probes with specificity for a different target nucleic acid. In another example, nucleic acid probes are coupled to the surface of a reaction chamber, such as a tip. For example, the interior surface of a tip may be coated with nucleic acid probes specific for a single target nucleic acid. Alternatively, the interior surface of a tip may be coated with two or more different nucleic acid probes specific for different target nucleic acids. When two or more different nucleic acid probes are coupled to the same interior tip surface, each of the different nucleic acid probes may be coupled at different known locations, such as forming distinct ordered rings or bands at different positions along the axis of a tip. In this case, multiple different nucleic acids may be analyzed in the same sample by drawing a sample up a tip and allowing nucleic acids contained in the sample to bind with the nucleic acid probes coated at successive positions along the tip. Binding events can then be visualized as described herein, with the location of each band in a banding pattern corresponding to a specific known nucleic acids.

In an embodiment, a sample may be assayed for a bacterial marker, such as the 16S ribosomal (small subunit) RNA (16S rRNA) or its gene (16S rDNA) by, for example, the nucleic acid amplification or probe-based assay described above. If a sample is determined to be positive for 16S rRNA or 16S rDNA, it is an indicator that the sample contains bacteria, and thus, that a subject who provided the sample may be suffering from a bacterial infection. Other bacterial markers which may be used include, for example, 23 S rRNA, rpoB, gyrB, dnaK, amoA, and mip genes, or their gene products. In another example, a sample may be assayed for a fungal marker, such as the internal transcribed spacer (ITS) region of the ribosomal cistron (as described, for example, in Schoch, et. al. Proc Natl Acad Sci USA. Apr. 17, 2012; 109(16): 6241-6246). Such organism class-based markers may provide information as to an overall type of infection a subject may have (e.g. bacterial, viral, or fungal) or the type of organism which is in a sample.

Other exemplary antigens and nucleic acids of pathogens useful for detecting a pathogen include, but are not limited to, antigens and nucleic acids of pathogens described herein. For example, retroviral nucleic acids and antigens include the HIV gag, pol, and env genes, and their gene products, the Nef protein, reverse transcriptase, and other HIV components. Illustrative examples of herpes simplex viral nucleic acids and antigens include, but are not limited to, genes encoding the immediate early proteins, glycoprotein D, and their gene products, and other herpes simplex viral components. Non-limiting examples of varicella zoster viral nucleic acids and antigens include genes encoding 9PI, gpII, and their gene products, and other varicella zoster viral components. Non-limiting examples of Japanese encephalitis viral nucleic acids and antigens include genes encoding the E, M-E, M-E-NS 1, NS 1, and NS 1-NS2A proteins, and their gene products, and other Japanese encephalitis viral components. Illustrative examples of hepatitis viral nucleic acid and antigens include, but are not limited to, genes encoding the S, M, and L proteins of hepatitis B virus, the pre-S antigen of hepatitis B virus, and their gene products, and other hepatitis (e.g., hepatitis A, B, and C) viral components. Illustrative examples of influenza viral nucleic acids and antigens include; but are not limited to, genes encoding hemagglutinin and neurarnimidase, and their gene products, and other influenza viral components. Illustrative examples of measles viral nucleic acids and antigens include, but are not limited to, the gene encoding the measles virus fusion protein and its gene product, and other measles virus components. Illustrative examples of rubella viral nucleic acid and antigens include, but are not limited to, genes encoding proteins E1 and E2, and their gene products, and other rubella virus components. Rotaviral nucleic acids and antigens include a gene encoding VP7sc and its gene products, and other rotaviral components. Illustrative examples of cytomegaloviral nucleic acids and antigens include, but are not limited to, a gene encoding the envelope glycoprotein B, and its gene products, and other cytomegaloviral components. Non-limiting examples of respiratory syncytial viral nucleic acids and antigens include genes encoding the RSV fusion protein, the M2 protein, and their gene products, and other respiratory syncytial viral components. Representative examples of rabies viral nucleic acids and antigens include, but are not limited to, genes encoding the rabies glycoprotein, rabies nucleoprotein, and their gene products, and other rabies viral components. Illustrative examples of papillomavirus nucleic acids and antigens include, but are not limited to, the genes encoding the L1 and L2 capsid proteins, the E6/E7 antigens associated with cervical cancers, and their gene products. See e.g. Fundamental Virology, Second Edition, eds. Fields, B. N. and Knipe, D. M., 1991, Raven Press, New York, for additional examples of viral antigens and nucleic acids.

Illustrative fungal nucleic acids and antigens that can be used in the compositions and methods of the present invention include, but are not limited to, *Candida* fungal antigen components; cryptococcal fungal antigens such as capsular polysaccharides and other cryptococcal fungal antigen components; *Histoplasma* fungal antigens such as heat shock protein 60 (HSP60) and other *Histoplasma* fungal antigen components; coccidiodes fungal antigens such as spherule antigens and other coccidiodes fungal antigen components;

and tinea fungal antigens such as trichophytin and other coccidiodes fungal antigen components, and any DNA or RNA encoding the antigens.

Bacterial nucleic acids and antigens which can be used in the compositions and methods of the invention include, but are not limited to: pertussis bacterial antigens such as pertussis toxin, filamentous hemagglutinin, pertactin, F M2, FIM3, adenylate cyclase and other pertussis bacterial antigen components; diphtheria bacterial antigens such as diphtheria toxin or toxoid and other diphtheria bacterial antigen components; tetanus bacterial antigens such as tetanus toxin or toxoid and other tetanus bacterial antigen components, streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components, pneumococcal bacterial antigens such as pneumolysin, pneumococcal capsular polysaccharides and other pnermiococcal bacterial antigen components; *Haemophilus influenza* bacterial antigens such as capsular polysaccharides and other *Haemophilus influenza* bacterial antigen components; anthrax bacterial antigens such as anthrax protective antigen and other anthrax bacterial antigen components; rickettsiae bacterial antigens such as rompA and other rickettsiae bacterial antigen component, and any DNA or RNA encoding the antigens. Also included with the bacterial nucleic acids and antigens described herein are any other bacterial, mycobacterial, mycoplasmal, rickettsial, or chlamydial nucleic acids and antigens.

Other parasitic nucleic acids and antigens which can be used in the compositions and methods of the invention include, but are not limited to: *Plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; *Leishmania major* and other leishmaniae antigens such as gp63, lipophosphoglycan and its associated protein and other leishmanial antigen components; toxoplasma antigens such as SAG-1, p30 and other toxoplasmal antigen components; schistosomae antigens such as glutathione-S-transferase, paramyosin, and other schistosomal antigen components; and *Trypanosoma cruzi* antigens such as the 75-77 kDa antigen, the 56 kDa antigen and other trypanosomal antigen components, and any DNA or RNA encoding the antigens.

The presence of an antigen or nucleic acid from a pathogen in a sample indicates that the pathogen is present in the sample, and thus, in the case of a sample from a human or animal, that the human or animal may be suffering from a disease caused by the pathogen. By subjecting a portion of a sample to an immunoassay, nucleic acid amplification reaction, nucleic acid probe-based assay, or any other suitable assay for a pathogen which may be in the sample, the assay result can provide information regarding whether a particular pathogen is present in the sample, and in certain embodiments, a quantitative measurement of the amount of pathogen in the sample.

Methods for Determining Susceptibility or Resistance to Antimicrobials

While the identification of a pathogen in a sample provides valuable information, in order to guide a potential treatment plan for a subject infected with a pathogen or for other pathogen management objectives, it may also be desirable to determine whether a pathogen is susceptible or resistant to one or more antimicrobials, such as antibiotics. Antimicrobial resistance is found where a population (or subpopulation) of a microorganism, such as a bacterium, acquires or exhibits resistance to one or more antimicrobials. Microorganisms that are resistant to treatment by multiple antimicrobials are termed to be "multi-drug resistant" and those microorganisms are termed to have or to exhibit "multi-drug resistance"; either term may be abbreviated by "MDR".

Resistance to one or more antimicrobials is observed, or exhibited, when a population of microorganisms survives (and typically continues to grow and multiply in number) despite the presence of an antimicrobial, or (in the case of MDR) despite the presence of multiple antimicrobials. For example, many antibiotic compounds include a β-lactam ring (a ring of four carbons); penicillin is an example of an antibiotic having a β-lactam ring. Many bacteria have β-lactamase enzymes which can cleave a β-lactam ring, and thus protect the bacteria against such antibiotics. Enzymes that can cleave a β-lactam ring, which are often found in Gram-negative bacteria and which may confer antibiotic resistance, include the TEM and ROB β-lactamase enzymes. In another example, drug-resistant *Haemophilus influenzae* bacteria may have the blaTEM or blaROB resistance gene (typically blaTEM-1, although blaTEM-2 and blaROB-1 and others are also found). Other examples of antimicrobial-resistance markers found in disease-causing organisms include the KPC resistance gene (found in *Klebsiella pneumonia* carbapenemas (KPC)), mecA and mecC resistance genes (responsible for resistance to β-lactam-containing antibiotics such as methicillin), and vancomycin resistance genes A and B (vanA and vanB) (found in, for example, vancomycin resistant Enterococci). Other examples of anti-microbial-resistant organisms include Methicillin-Resistant *Staphylococcus aureus* (MRSA), vancomycin-intermediate *S. aureus* (VISA), vancomycin-resistant *S. aureus* (VRSA), bacteria (e.g., Enterobacteriaceae) having extended spectrum beta-lactamase (ESBL), and Multidrug-resistant *A. baumannii* (MRAB). Drug-resistant target organisms, including MDR target organisms, may be identified by detecting antimicrobial resistance-conferring nucleic acid markers, protein markers, other markers, or combinations thereof.

Various methods may be used to test for a pathogen's response to one or more antimicrobials. For example, a sample obtained from a subject suspected of having an infection with a pathogen may be subjected to a nucleic acid-based test to assay the sample for the presence of an antimicrobial resistance-conferring gene, for the deletion of a gene which results in antimicrobial resistance, or for a mutation (e.g. a point mutation, a single-nucleotide polymorphism (SNP), or a multi-nucleotide mutation) which confers antimicrobial resistance. Such nucleic acid-based tests may include, for example, nucleic acid amplification reactions and nucleic acid probe-based assays described above. In an example, a nucleic acid-based test to test for a mutation may be performed as described in WO 2015/076919, which is hereby incorporated by reference in its entirety for all purposes.

For example, to detect the presence or absence of a particular nucleotide of interest in a target nucleic acid (e.g. in the case of a mutation or SNP), a first or second primer may be selected which selectively binds to a region in a target nucleic acid which includes or is adjacent to the nucleotide of interest. The primer may be designed such that it selectively either: i) binds to the region when the region contains the nucleotide of interest, or ii) does not bind to the region when the region contains the nucleotide of interest. A method as described herein may be performed with the selected primer, and the outcome of the amplification reaction may provide information regarding the presence or absence of the nucleotide of interest in the target nucleic acid. For example, if the template-binding region of a first primer is designed to have a nucleotide sequence which is complementary to a sequence in the target nucleic acid which includes a particular nucleotide of interest (e.g. a mutation), successful amplification of the target nucleic acid with the selected primer from a sample may indicate that the sample contains a target nucleic acid having the particular nucleotide of interest. In some embodiments, a primer used for analysis of a nucleotide of interest in a target nucleic acid may contain a critical nucleotide (i.e. a nucleotide which corresponds to the same position of a nucleotide of interest in the target nucleic acid) at the 3' terminus of the primer. In such a case, the hybridizing of the 3' terminal nucleotide of the primer may be dependent on the presence of the nucleotide of interest in the target nucleic acid. If the 3' terminal nucleotide of the primer does not hybridize with a nucleotide in the target nucleic acid (e.g. due to a mismatch between the nucleotides), the mismatch may significantly impair a nucleic acid polymerase from synthesizing an extension product from the primer. Accordingly, in some embodiments, a primer having a 3' terminal nucleotide which corresponds to a nucleotide of interest may be useful for determining the presence or absence of a particular nucleotide in a target nucleic acid. In such embodiments, in some situations the critical nucleotide at the 3' terminus of the primer may be selected to be complementary to the nucleotide of interest in the target nucleic acid, and in some other situations the critical nucleotide at the 3' terminus of the primer may be selected to be non-complementary the nucleotide of interest in the target nucleic acid. The nucleotide of interest may represent, for example, a wild-type form, a mutant form, or a polymorphism of a target nucleic acid.

In other embodiments, a particular nucleotide of interest in a target nucleic acid (e.g. a mutation or SNP) may be detected by selecting primers such that the nucleotide of interest is present in the target nucleic acid in a region which is not complementary to a template-binding region of a first or second primer. For example, the nucleotide of interest may be approximately in the middle of a target nucleic acid sequence. In embodiments, the nucleotide of interest may be in an "internal motif," a portion of the target nucleic acid strand to which the tail region of one primer of a primer pair to amplify the target nucleic acid provided herein is complementary, and which has the same or a similar nucleotide sequence as the tail region of the other primer of the primer pair. When a nucleotide of interest is in an internal motif, in embodiments, a primer pair may be prepared to contain a nucleotide sequence in the tail region of the primers which is complementary to an internal motif or the complement thereof, and which may be used to assay for the presence or absence of the nucleotide of interest in the internal motif in the target sequence. The temporary hybridizing of a nucleotide sequence in the tail region of a primer to an internal motif in an extension product of that primer may increase the rate of a reaction provided herein. In some circumstances, the greater the affinity of a nucleotide sequence in the tail region of a primer to the internal motif in an extension product of that primer, the faster the reaction may occur. Also, typically, the greater the number of nucleotides in the nucleotide sequence in the tail region of the primer which can bind to nucleotides in the internal motif in the extension product of the primer, the greater the affinity of the nucleotide sequence in the tail region of the extension product for the internal motif in the extension product. Thus, in embodiments, the presence or absence of a nucleotide of interest in a target sequence may be determined through the use of primers which have a nucleotide sequence in the tail region of the primer which can bind to the internal motif in the target sequence or a complement thereof, and which, within the tail region, do or do not have a nucleotide which specifically binds with the particular nucleotide of interest in the internal motif or its complement. Typically, the reaction will occur faster when the nucleotide sequence in the tail region of a primer contains a nucleotide which is complementary to the nucleotide in the extension product of that primer which corresponds to the nucleotide of interest in the target, than when the relevant nucleotide in the tail region of the primer is not complementary to the nucleotide in the extension product of that primer which corresponds to the nucleotide of interest in the target.

In another example of a method which may be used to test for a pathogen's response to one or more antimicrobials, a pathogen contained in a sample obtained from a subject may be provided with an opportunity to grow in a microorganism growth medium in the presence of an antimicrobial, and the growth of the pathogen in the presence of the antimicrobial may be assessed. In such examples, typically, the pathogen is a bacterium. However, the method may also be applied to other pathogens, such as fungi, protists, parasites, or viruses. As used herein, the growth of a pathogen in the presence of an antimicrobial may be referred to as "antimicrobial-present growth." In situations wherein a pathogen is susceptible to an antimicrobial, typically the pathogen will have substantially less growth (including no growth) when it is cultured under growth conditions in the presence of the antimicrobial, as compared to when it is cultured under the same conditions without the antimicrobial. Thus, if a pathogen is cultured in a microorganism growth medium in the presence of an antimicrobial to which the pathogen is resistant, the pathogen will still have a high level of antimicrobial-present growth. In contrast, if a pathogen is cultured in a microorganism growth medium in the presence of an antimicrobial to which the pathogen is susceptible, the pathogen will have a low level of (or no) antimicrobial-present growth.

As used herein, "culturing" refers to maintaining a microorganism in conditions sufficient to support the growth of the microorganism. Also, references herein to conditions sufficient to support the growth of a pathogen in a microorganism growth medium and the like (e.g. "growth conditions") refer to conditions that are generally sufficient to support the growth of the pathogen in the medium, if no antimicrobial is present in the mixture or if an antimicrobial is present in the medium, but the pathogen is resistant to the antimicrobial. For example, if a pathogen readily grows on chocolate agar at a temperature of 37° C., the condition of chocolate agar and 37° C. are conditions sufficient to support the growth of the pathogen. However, if an antimicrobial is present in a microorganism growth medium and the pathogen is not resistant to the antimicrobial, the pathogen may not be able to grow or may have reduced growth in conditions which are otherwise sufficient to support the growth of the pathogen. Thus, references herein to conditions sufficient to support the growth of a pathogen do not reflect the possible presence of antimicrobials in a mixture, or of possible resistance of the pathogen to an antimicrobial. If a pathogen is cultured in conditions sufficient to support the growth of a pathogen, but an antimicrobial is present in the medium, and the pathogen is not resistant to the antimicrobial, the pathogen may not be able to grow or may have reduced growth. Conversely, if a pathogen is cultured in conditions sufficient to support the growth of a pathogen, even if an antimicrobial is present in the medium, if the pathogen is resistant to the antimicrobial, the pathogen may still be able to grow normally or only have slightly impaired growth, despite the presence of the antimicrobial in the medium.

Traditional methods for assessing growth of a pathogen in the presence of an antimicrobial typically involve lengthy culture times (e.g. culture time of at least 48, 72, or 96 hours), before an accurate measurement of antimicrobial-present growth for a pathogen in response to an antimicrobial could be obtained. In embodiments provided herein, antimicrobial-present growth for a pathogen in response to an antimicrobial can be obtained more rapidly than traditional methods, such as within 24, 22, 20, 18, 16, 14, 12, 10, 9, 8, 7, 6, 5, 4, 3, 2, or 1 hour of the initiation of culture of a pathogen in the presence of an antimicrobial under conditions sufficient to support antimicrobial-present growth (i.e. in an appropriate growth medium and at a suitable temperature for pathogen growth).

In embodiments provided herein, a variety of different methods may be used to rapidly assess antimicrobial-present growth of a pathogen in the presence of an antimicrobial. For example, a pathogen may be cultured in a liquid growth medium containing an antimicrobial of interest, and the optical density of the liquid growth medium may be measured at one or more time points after the initiation of the culture. The optical density may be measured, for example, in a spectrophotometer at a wavelength at or near 600 nm. As a pathogen increases in number in a liquid growth medium, the optical density of the sample increases. In another example, a pathogen in a growth medium containing an antimicrobial may be assessed for a measurement (e.g. percentage, ratio, absolute number, etc.) of pathogen cells which are dividing at one or more time points after the initiation of culture of the pathogen with an antimicrobial in the growth medium. Pathogen cells may be assessed for cell division by various methods, such as by measuring by cytometry the morphology of cells (e.g. to observe cell fission or enlarged size prior to division) or by assessing cells for one or more markers indicative of cell division (e.g. by labeling pathogen cells with an antibody against a protein which is selectively expressed during cell division (e.g. the tubulin homolog FstZ); such labeling of cells may be monitored, for example, by cytometry). In another example, a pathogen in a growth medium containing an antimicrobial may be assessed for a measurement (e.g. percentage, ratio, absolute number, etc.) of pathogen cells which are replicating or have replicated DNA at one or more time points after the initiation of culture of the pathogen with an antimicrobial in the growth medium. The DNA content of cells may be measured, for example, by staining cells with a nucleic acid dye (e.g. Hoechst dyes, DAPI, ethidium bromide, SYBR dyes, etc.).

In another example, a pathogen in a microorganism growth medium containing an antimicrobial may be assessed for one or more biochemical characteristics at one or more time points after the initiation of culture with an antimicrobial in the microorganism growth medium (e.g. a level of one or more proteins, small molecules, or lipids, or a level of cell respiration or metabolic activity). Such biochemical characteristics may provide information regarding the pathogen's response to an antimicrobial. In an embodiment, the metabolic activity of a pathogen may be assayed in the presence of an antimicrobial to determine the resistance or susceptibility of the pathogen to the antimicrobial. For example, metabolic activity of a pathogen may be assayed by culturing the pathogen in a microorganism growth medium in the presence of an antimicrobial and a metabolic indicator, and detecting a metabolic product. As used herein, a "metabolic indicator" refers to a substance that is capable of being metabolized by a metabolically active pathogen or a cell infected with a pathogen (eg. a virus) to produce a metabolic product. A "metabolic product," as used herein, refers to any intermediate or product produced as a result of metabolism of the metabolic indicator. Detection of the metabolic product indicates that the pathogen is antimicrobial resistant. In a particular embodiment, the metabolic product generates a detectable signal, such as color, fluorescence, or luminescence. Examples of metabolic indicators include, but are not limited to, resazurin, 5-cyano-2,3-ditolyl tetrazolium chloride (CTC), carboxyfluorescein diacetate succinimidyl ester (CFDA-SE), and luciferin. Examples of the respective metabolic indicators include, but are not limited to, resorufin, CTC formazan, carboxyfluorescein succinimidyl ester (CF SE), and oxyluciferin.

Resazurin (7-hydroxy-3H-phenoxazin-3-one 10-oxide) is a blue dye that is weakly fluorescent until it is irreversibly reduced to a pink colored and highly red fluorescent resorufin. Metabolically active, living cells are able to reduce resazurin to resorufin, which can be detected colorimetrically or by measuring the fluorescence at about 590 nm. The fluorescent output is proportional to the number of viable cells and may be measured with a spectrophotometer. Thus, antimicrobial resistance may be detected by fluorescence or change in color of the assay, and antimicrobial sensitivity may be detected by low or no fluorescence or no change in color of the assay. CTC is a monotetrazolium redox stain that produces a red-fluorescent CTC formazan when it is chemically or biologically reduced and is detectable when excited by blue light (at wavelength 480 nm). CFDA-SE is a cell permeable, non-fluorescent dye that produces a fluorescent CFSE when cleaved by intracellular esterase enzymes. Luciferin is a small molecule converted to a luminescent oxyluciferin in the presence of ATP and luciferase enzyme.

In an embodiment, a sample obtained from a subject may be pre-cultured in the absence of the antimicrobial and metabolic indicator as described above to increase the concentration of the pathogen in the sample. Alternatively, the sample may not need to be pre-cultured if the sample contains a sufficient amount of the pathogen. The sample may be diluted and then cultured in an appropriate microorganism growth medium containing an antimicrobial and a metabolic indicator. In an embodiment, the sample may be cultured in the microorganism growth medium in the presence of the antimicrobial and the metabolic indicator for about 1 hr to about 8 hrs. In another embodiment, the sample may be cultured for about 2 hrs to about 6 hrs. In a further embodiment, the sample may be cultured for about 10, 20, or 30 minutes, or greater, to about 1, 2, 3, 4, 5, 6, 7, 8, 9, or 10 hrs, or less. The sample may be cultured at about 37° C.

In methods provided herein, the total reaction volume may be between about 1 µl to about 200 µl. In a particular embodiment, the total reaction volume may be about 10 µl to about 100 µl. The concentration of a metabolic indicator, such as resazurin, in the total reaction may be about 10, 20, 30, 40, 50, 60, 70, 80, 90, or 100 µM. In another embodiment, the metabolic indicator concentration may be between about 10 to about 100 µM. In a particular embodiment, the metabolic indicator concentration may be between about 20 to about 80 µM. In an embodiment, the methods described herein may detect about 1, $10^1$, $10^2$, $10^3$, $10^4$, $10^5$, $10^6$, $10^7$, or $10^8$ pathogens/reaction. In another embodiment, the methods may detect between about $10^1$ to about $10^5$ pathogens/reaction.

In a particular embodiment, a sample may be contacted with an antimicrobial, and the pathogen may assessed for one or more markers of cell death at one or more time intervals after the introduction of the antimicrobial to the sample. Markers of cell death may be, for example, the expression of one or more biochemical markers in a cell, changes in chromosome structure, or the development of a particular cell morphology. Biochemical markers related to cell death may be, for example, proteins (e.g. proteases such as caspases), nucleic acid (e.g. fragmented DNA), or small molecules (e.g. reactive oxygen species (ROS)). In embodiments, the level of certain biochemical markers may increase or decrease as a cell is dying (i.e. the level of some markers may increase as a cell is dying/dead and the level of some markers may decrease as a cell is dying/dead). In embodiments, pathogens may be assessed for one or more changes associated with cell death at one or more time points after the exposure of the pathogen to an antimicrobial. This information may be used to determine if the pathogen is resistant or susceptible to an antimicrobial. In embodiments, pathogens which have been exposed to a particular antimicrobial may be stained with one or more dyes, and images of the stained pathogens may be obtained. Through pattern recognition methods, information from images of a test pathogen sample may be compared to information from images of pathogens known to be resistant to or susceptible to the antimicrobial being tested. Based on this analysis, the susceptibility or resistance of the pathogen to an antimicrobial of interest may be determined very rapidly.

In embodiments, any of the above measurements for antimicrobial-present growth of a pathogen in response to an antimicrobial may be performed within 24, 22, 20, 18, 16, 14, 12, 10, 9, 8, 7, 6, 5, 4, 3, 2, or 1 hour of the initiation of culture of a pathogen in the presence of an antimicrobial under conditions sufficient to support antimicrobial-present growth. Similarly, in embodiments, with systems and methods provided herein, the antimicrobial-resistance status of a pathogen can be determined within 24, 22, 20, 18, 16, 14, 12, 10, 9, 8, 7, 6, 5, 4, 3, 2, or 1 hour of the initiation of processing a sample containing a pathogen for pathogen antimicrobial resistance.

Detecting the Presence of a Pathogen and Determining Antimicrobial Resistance/Susceptibility of the Pathogen In any of the methods described herein, a first sample obtained from a subject may be used to assay for the presence of a pathogen and a second sample obtained from the subject may be used to assay for antimicrobial resistance or susceptibility of the pathogen. Alternatively, in any of the methods described herein, a first portion of a sample may be used to assay for the presence of a pathogen and a second portion of a sample used to assay for antimicrobial resistance or susceptibility of the pathogen.

In an embodiment, a first portion of a sample or a first sample may be used to assay for the presence of a nucleic acid of a pathogen in the sample by subjecting the sample to a nucleic acid amplification assay, such as by PCR, RT-PCR, or according to a method provided in WO 2014/145291, WO 2014/145296, or WO 2014/145298, and a second portion of the sample or a second sample may be used to assay for the presence of an antimicrobial resistance gene or mutation in the pathogen, such as by PCR, RT-PCR, or according to a method provided in WO 2014/145291, WO 2014/145296, WO 2014/145298, or WO 2015/076919.

In another embodiment, a first portion of a sample or a first sample may be used to assay for the presence of a nucleic acid of a pathogen in the sample by subjecting the sample to a nucleic acid amplification assay, such as by PCR, RT-PCR, or according to a method provided in WO 2014/145291, WO 2014/145296, or WO 2014/145298, and a second portion of the sample or a second sample may be used to assay for antimicrobial resistance or susceptibility of the pathogen by assaying for the metabolic activity of the pathogen in the sample in the presence of the antimicrobial. In a particular embodiment, the nucleic acid of a pathogen is a bacterial marker (eg. 16S rRNA) and the metabolic activity of a pathogen is assayed using a metabolic indicator (resazurin).

In an embodiment, a first portion of a sample or a first sample may be used to assay for the presence of a nucleic acid of a pathogen in the sample by subjecting the sample to a nucleic acid probe-based assay, and a second portion of the sample or a second sample may be used to assay for the presence of an antimicrobial resistance gene or mutation in the pathogen, such as by PCR, RT-PCR, or according to a method provided in WO 2014/145291, WO 2014/145296, WO 2014/145298, or WO 2015/076919.

In an embodiment, a first portion of a sample or a first sample may be used to assay for the presence of a nucleic acid of a pathogen in the sample by subjecting the sample to a nucleic acid probe-based assay, and a second portion of the sample or a second sample may be used to assay for antimicrobial resistance or susceptibility of the pathogen by assaying for the metabolic activity of the pathogen in the sample in the presence of the antimicrobial. In a particular embodiment, the nucleic acid of the pathogen is a bacterial marker (eg. 16S rRNA) and the metabolic activity of a pathogen is assayed using a metabolic indicator (eg. resazurin).

Any other combination of the assays disclosed herein may be used to detect the presence of a pathogen and to determine antimicrobial resistance or susceptibility of the pathogen. In embodiments, the assay for detecting the presence of a pathogen and the assay for determining antimicrobial resistance or susceptibility of the pathogen may be performed in parallel, or alternatively, sequentially. For example, the assay for detecting the presence of a pathogen may be performed first and depending on the results, the assay for determining antimicrobial resistance or susceptibility of the pathogen may then be performed. In other embodiments, any part of an assay for detecting the presence of a pathogen may be performed simultaneously with any part of an assay for determining antimicrobial resistance or susceptibility of the pathogen.

Sample Processing System and Device

In embodiments, the methods of the present invention may be performed in a sample processing device. A sample, cartridge, system, or method of sample processing provided herein may have any of the characteristics described in U.S. Pat. No. 8,088,593, WO 2014/127379, U.S. Pub. No. 2015/0072362, or WO 2015/035260, each of which is hereby incorporated by reference in its entirety for all purposes.

Embodiments provided herein may be described with reference to FIG. 1. A sample 110 may be introduced into a sample processing device 100.

The sample processing device 100 may be an instrument which contains one or more hardware components within a housing for processing a sample, such as sample handling systems, including fluid handling systems, heating elements, centrifuges, detectors including but not limited to photodiodes, photomultiplier tubes (PMTs), spectrophotometers, optical sensors (e.g., for luminescence, fluorescence, absorbance, or colorimetry), cameras, and cytometers, pipettes, thermal control units, and controllers. The term "sample handling system," as used herein, refers to a device or system configured to aid in sample imaging, detecting, positioning, repositioning, retention, uptake, and deposition. In an example, a robot with pipetting capability is a sample handling system. In another example, a pipette which may or may not have (other) robotic capabilities is a sample handing system. A sample handling system may transport any type of sample, including but not limited to bodily fluids, secretions, or tissue samples. A sample handling system may be capable of handling fluids, solids, or semi-solids. A sample handling system may be capable of accepting, depositing, and/or moving a sample, and/or any other substance within the device that may be useful and/or necessary for sample processing within the device. A sample handling system may be capable of accepting, depositing, and/or moving a container or vessel (e.g., assay unit, reagent unit) that may contain a sample, and/or any other substance within the device. In some situations, a sample handling system is a fluid handling system. Any description herein of a fluid handling system may also apply to other sample handling systems, and vice versa. The fluid handling system may comprise pumps and valves of various types or pipettes, which, may comprise but not be limited to a positive displacement pipette, air displacement pipette and suction-type pipette. A fluid handling system may include a tip. For example, a pipette tip may be removably connected to a pipette. The tip may interface with a pipette nozzle. A sample processing device 100 may have any of the features as described in, for example, WO 2014/127379, U.S. Pat. No. 8,088,593, or U.S. Pat. No. 8,435,738, all of which are hereby incorporated by reference in their entirety for all purposes.

The sample 110 may be introduced into the sample processing device 100 by any suitable structure or method. In embodiments, a sample 110 may be directly introduced into the sample processing device 100. In other embodiments, a sample 110 may be first introduced into a cartridge, and the cartridge may then be introduced into the sample processing device. A cartridge may contain reagents, other samples, or other components used for sample processing. In embodiments, a cartridge may have any of the features of a cartridge described in WO 2014/127379, U.S. Pat. No. 8,088,593, or U.S. Pat. No. 8,435,738, or a sample may be introduced into a sample processing device by any method described in these documents.

Figure 2:
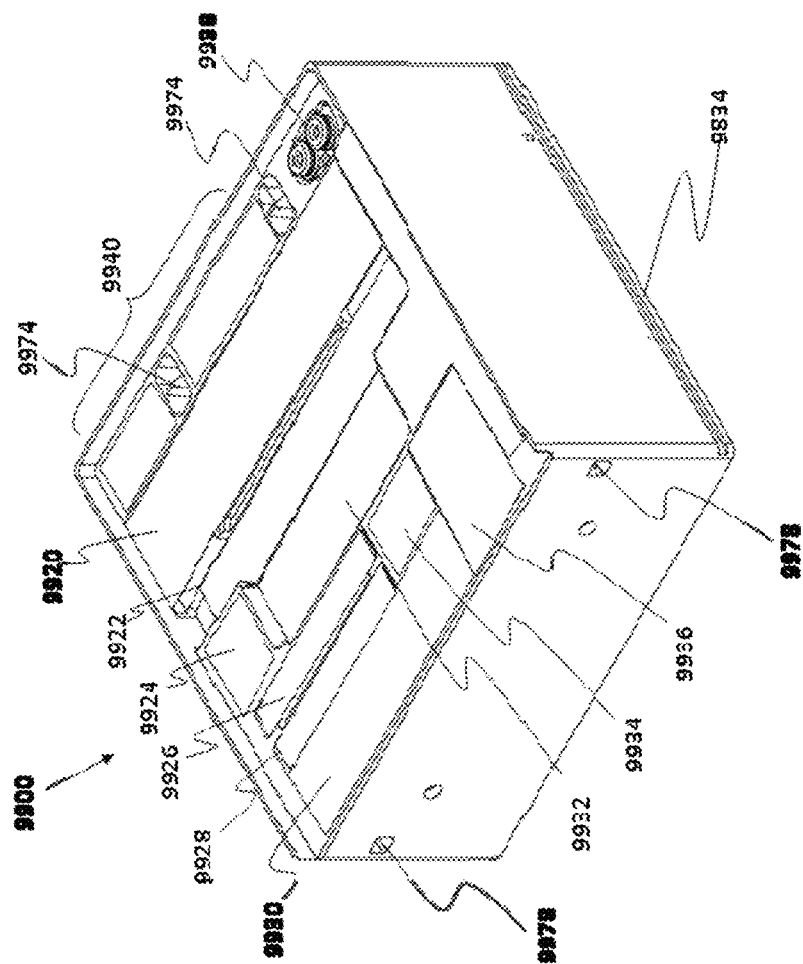
FIGS. 2 and 3 show at least some embodiments of cartridges as described herein.

Referring now to FIG. 2, one non-limiting example of a cartridge 9900 will now be described. This embodiment shows that there may be a plurality of different regions 9920 to 9940 on the cartridge 9900 to provide different types of devices, tips, reagents, reaction locations, or the like. In one non-limiting example, one of these regions on the cartridge 9900 may contain at least one vessel or container in one of these regions that may house one or more antimicrobial or other drug as described herein. The mix of these components depends on the types of assays to be performed using the cartridge 9900. By way of nonlimiting example, the cartridge 9900 may have regions to accommodate one or more sample containers, pipette tips, microscopy cuvette, large volume pipette tip, large volume reagent well, large volume strip, cuvette with a linear array of reaction vessel, round vessels, cap-removal tip, centrifuge vessel, centrifuge vessel configured for optical measurement(s), and/or nucleic acid amplification vessels. Any one of the foregoing may be in the different regions 9920 to 9940. Some may arrange the tips and vessels in arrays similar to those of the cartridges shown in commonly assigned WO 2014/127379, U.S. Pat. No. 8,088,593, or U.S. Pat. No. 8,435,738, each fully incorporated herein by reference for all purposes.

By way of non-limiting example, the reagents may also vary in the cartridge and may be selected to include at least those desired to perform at least two or more types of assay panels such as but not limited to a panel for potential pathogens, a lipid panel or a chem14 panel or other combination of two or more different laboratory testing panels. For example, some cartridges may have reagents, diluents, and/or reaction vessels to support at least two different assay types from nucleic acid amplification, nucleic acid probe-based assay, metabolic/biochemical assay, general chemistry, immunoassay, or cytometry.

Any one or more of the components of the cartridge may be accessible by a sample handling system or fluid handling system of the sample processing device. The different zones in the cartridge may be configured to match the pitch of the pipette heads used in the system. Optionally, some zones are configured to be at pitches that are multiples of or fractions of the pitch of the pipette heads. For example, some components of the cartridge are at ⅓× of the pitch, others at ½× of the pipette pitch, others at a 1× pitch, others at a 2× pitch, while still others at a 4× pitch.

Referring still to FIG. 2, it should be understood that there may be components located at one plane of the cartridge while others are located at lower or higher planes. For example, some components may be located below a cuvette or other component. Thus, once the upper component is removed, the lower components become accessible. This multi-layer approach provides for greater packing density in terms of components on a cartridge. There may also be locating features on the cartridge 9900 such as but not limited to rail 9834 that is configured to engage matching slot on the cartridge receiving location in the system. The cartridge may also have registration features (physical, optical, or the like) that allow the system to accurately engage components of the cartridge once the cartridge is recognized by the system. By way of non-limiting example, although components may be removed from the cartridge 9900 during assay processing, it is understood that some embodiments may permit the return of all components back to the cartridge for unified disposal. Optionally, some embodiments of the system may have disposal areas, containers, chutes, or the like to discard those components of the cartridge not returned to the cartridge prior to ejecting the cartridge from the system. In some embodiments, these areas may be dedicated areas of the system for receiving waste.

Figure 3:
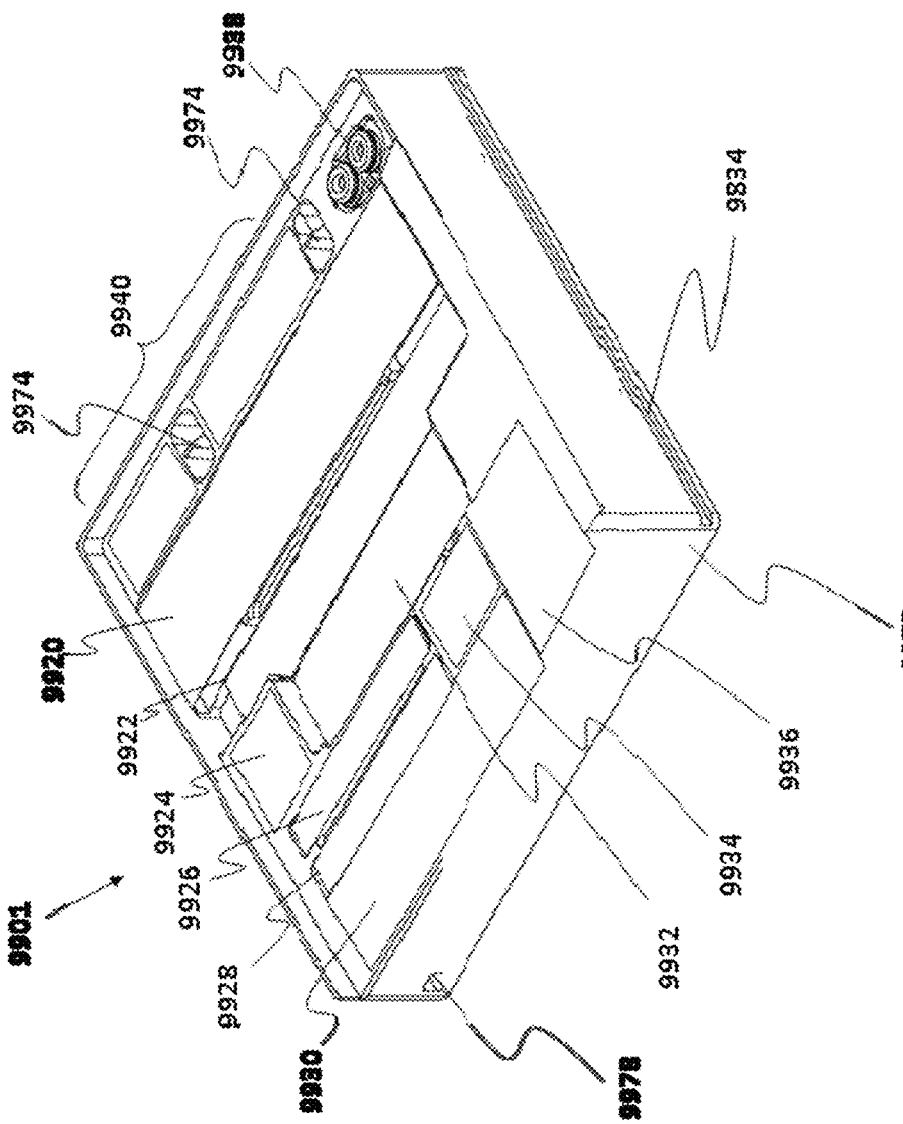

Referring now to FIG. 3, another embodiment of the cartridge will now be described. This embodiment is similar to that of FIG. 2 except that this one uses a reduced height cartridge 9901 wherein the sidewalls have a reduced vertical height. This provides for less material use for the disposable and brings the reaction vessels and/or reagents. Again, in one non-limiting example, one of these regions on the cartridge 9901 may contain at least one vessel or container in one of these regions that may house one or more antimicrobial or other drug as described herein.

Figure 4A:
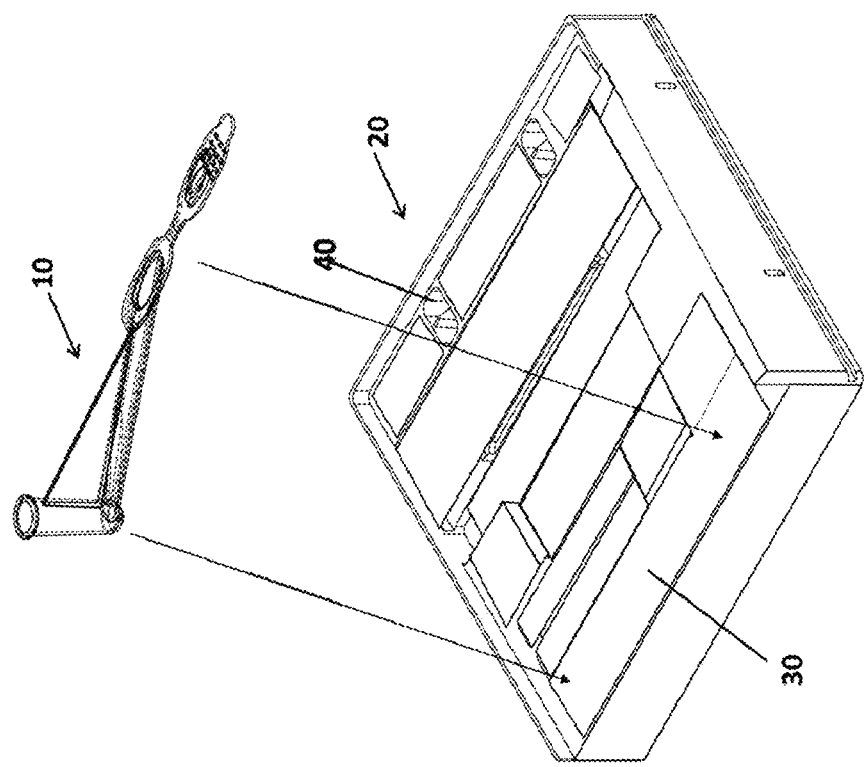
FIGS. 4A, 4B, and 4C show exemplary cartridges and vessels for holding a swab.

In another embodiment, FIG. 4A shows an exemplary vessel for holding a swab (a swab container) and an exemplary cartridge which includes receptacles (cavities and wells for, e.g., a swab container, reagent vessels, assay units, mixing vessels, transport units, pipette tips, waste vessels, and sample collection vessels), and is configured to hold reagent vessels, reaction vessels, and other vessels and implements. A swab may be used to obtain a sample from a subject. A subject may obtain the sample using the swab by him or herself, or a health professional (e.g. a phlebotomist, nurse, or doctor) may use a swab to obtain a sample from a subject. A swab may be used to obtain a sample such as from a subject's nose, throat, mouth, ear, skin, or other body region. Arrows leading away from the swab container indicate how the swab container may be placed into a receptacle in the cartridge.

Figure 4B:
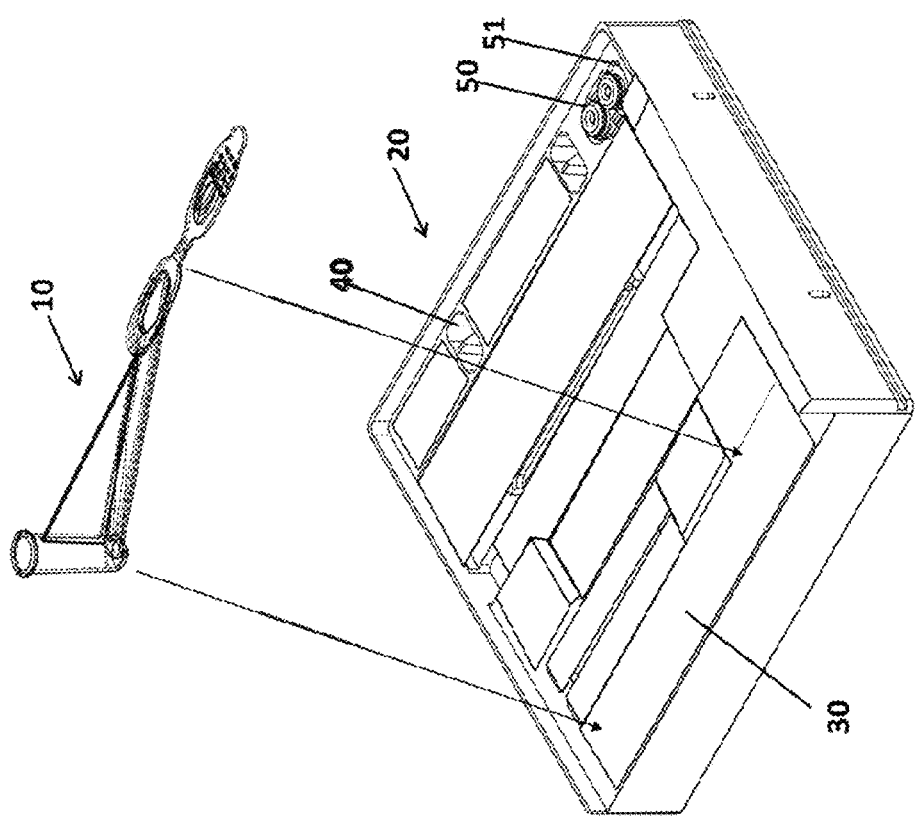

FIG. 4B shows an exemplary swab container (configured for holding a swab) and an exemplary cartridge (which includes cavities and wells for reagents and vessels, and is configured to hold reagent vessels, reaction vessels, and other vessels and implements). In addition to the cavities and wells configured to hold reagent vessels, reaction vessels, and other vessels and implements as shown in the embodiment of FIG. 4A, the exemplary cartridge shown in FIG. 4B includes cavities and wells suitable for holding other sample vessels, e.g., blood or urine sample vessels, in addition to swab containers. Arrows leading away from the swab container indicate how the swab container may be placed into a receptacle in the cartridge.

Figure 4C:
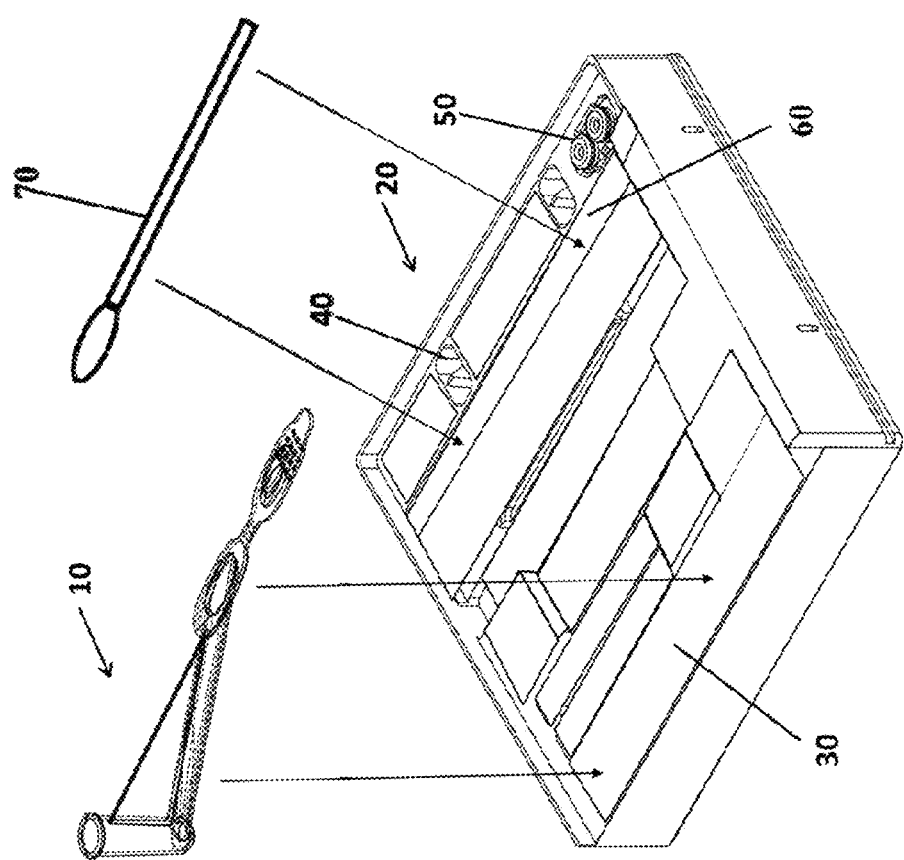

FIG. 4C shows an exemplary swab container, and an exemplary cartridge which includes cavities and wells for holding a swab and a swab container, as well as cavities and wells configured to hold reagent vessels, reaction vessels, and other vessels and implements (which may optionally include other sample vessels, e.g., blood or urine sample vessels). Arrows leading away from the swab indicate how the swab may be placed into a swab receptacle in the cartridge. Arrows leading away from the swab container indicate how the swab container may be placed into a swab container receptacle in the cartridge.

As shown in FIG. 4A, FIG. 4B, and FIG. 4C, a vessel for holding a swab may be loaded onto a cartridge, where it may be retained until needed for processing; the cartridge may be loaded onto a sample processing device, thereby loading the swab (and any other samples or sample containers on the cartridge as well). FIGS. 4A, 4B, and 4C show exemplary containers for holding a swab (a swab container) and exemplary cartridges (which includes cavities and wells for reagents and vessels, and is configured to hold one or more of reagent vessels, assay units, mixing vessels, pipette tips, transport units, and other vessels and implements, including other sample vessels, e.g., blood or urine sample vessels). Arrows leading away from the swab container indicate how the swab container may be placed into a receptacle in the cartridge.

As shown in FIG. 4A, a vessel for holding a swab (a swab container 10) may be loaded onto a cartridge 20 by placement into a receptacle 30. The cartridge 20 as shown also includes cavities and wells 40 for receiving and holding reagents and vessels. A swab container 10 may contain a swab in place within the swab container 10, or may be loaded onto a cartridge without a swab in place within the swab container 10.

As shown in FIG. 4B, a swab container 10 may be loaded onto a cartridge 20 by placement into a receptacle 30. The cartridge 20 as shown also includes cavities and wells 40 for receiving and holding reagents and vessels. In the embodiment shown in FIG. 4B, the cartridge 20 also includes a sample collection vessel 50, which may hold, e.g., blood, urine, or other sample. The arrows leading away from the swab container 10 indicate how the swab container 10 may be placed into a receptacle 30 in the cartridge 20. Thus, as shown in FIG. 4B, a swab container 10 may be loaded onto a cartridge 20, where it may be retained until needed for analysis; the cartridge 20 may be loaded onto an analysis device or analysis system, thereby loading the swab container 10 (and any sample container or sample containers that are also in place on the cartridge 20 as well). A cartridge 20 may have a receptacle 30. As shown in FIG. 4B, a swab container 10 may be loaded onto a cartridge 20 by placement into a receptacle 30. The cartridge 20 as shown also includes cavities and wells 40 for receiving and holding reagents and vessels. The cartridge 20 as shown also includes a sample collection vessel 50, which may hold, e.g., blood, urine, sputum, or other sample. The sample collection vessel 50 is shown in position in a sample collection vessel receptacle 51 in the cartridge 20. The arrows leading away from the swab container 10 indicate how the swab container 10 may be placed into a receptacle 30 in the cartridge 20.

As shown in FIG. 4C, a swab container 10 may be loaded onto a cartridge 20 by placement into a receptacle 30. The cartridge 20 as shown also includes cavities and wells 40 for receiving and holding reagents and vessels. As shown in the embodiment of FIG. 4C, the cartridge 20 includes a swab receptacle 60 configured to hold a swab 70. In embodiments (e.g., in the embodiment illustrated in FIG. 4C) a cartridge 20 having a swab receptacle 60 may optionally include a sample collection vessel 50, which may hold, e.g., blood, urine, or other sample. Such a swab 70 may be held in swab receptacle 60 prior to its use in collecting a sample. In embodiments, a swab 70 may be placed within a swab container 10 after collection of a sample with swab 70. In the embodiment shown in FIG. 4C, swab container 10 may be loaded onto a cartridge without a swab in place within the swab container 10 prior to use of swab 70, and swab container 10 may be replaced in a receptacle 30, holding swab 70 within swab container 10 after collection of a sample by swab 70.

In embodiments, as cartridge may contain one or more antimicrobial. Within a cartridge, an antimicrobial may be provided in an isolated structure (e.g. a fluidically isolated well or vessel), so that the antimicrobial initially is not in direct contact with other reagents or samples in the cartridge. Once a cartridge is inserted into a sample processing device, the antimicrobial may be brought into direct contact with one or more other reagents or samples in the cartridge (e.g. by a fluid handling system). An antimicrobial may be in any suitable form, such as dried, in solution, or in suspension. A cartridge may contain, for example, at least 1, 2, 3, 4, 5, 6, 7, 8, 9, 10, 15, or more different specific antimicrobial compounds or different classes of antimicrobial compounds. In certain embodiments, an antimicrobial may be in a cartridge pre-mixed in a microorganism growth medium or other suitable material.

In embodiments, once a sample 110 is introduced into a sample processing device 100 (as shown in FIG. 1), the sample 110 may be processed in multiple different ways within the sample processing device 100. For example, within the sample processing device 100, a sample 110 may be divided into at least two different fluidically isolated portions (e.g. at least a first portion and a second portion) by a fluid handling system. The first portion may be used for at least a first laboratory test or part thereof, and the second portion may be used for at least a second laboratory test or part thereof. In embodiments, a first portion of a sample may be used in a first laboratory test to determine whether a particular pathogen of interest is present in the sample, and a second portion of the sample may be used in a second laboratory test may be to determine whether a pathogen in a sample is resistant or susceptible to an antimicrobial.

In embodiments, at least two samples may be introduced into a sample processing device and each sample may be processed different in the sample processing device. For example, a first sample may be used for at least a first laboratory test or part thereof, and a second sample may be used for at least a second laboratory test or part thereof. In embodiments, a first sample may be used in a first laboratory test to determine whether a particular pathogen of interest is present in the sample, and a second sample may be used in a second laboratory test may be to determine whether a pathogen in a sample is resistant or susceptible to an antimicrobial. In embodiments, the cartridge may contain at least 1, 2, 3, 4, 5, 6, 7, 8, 9, 10, or more samples. The one or more samples may be provided in separate, fluidically isolated vessels in the cartridge, and introduced into the sample processing device.

In embodiments, an assay to test for the presence of a pathogen in a sample and/or response of a pathogen to an antimicrobial may occur via an automated process within a sample processing device 100 provided herein. In embodiments, a portion of a sample may be directly used to test for a pathogen in the sample's response to an antimicrobial. In other embodiments, a pathogen in a sample may first be enriched or concentrated within the sample processing device (e.g. by physical methods, such as use of an antibody-based capture surface for the pathogen, culturing the pathogen, centrifugation to move pathogens towards the bottom of a tube containing a liquid suspension of the pathogen, or filtration to capture the pathogens from a liquid suspension of the pathogen), and the enriched or concentrated pathogen may be used to test for the presence of the pathogen or pathogen's response to an antimicrobial. Thus, the sample processing device may comprise components for enriching or concentrating the pathogen, such as a centrifuge. Additionally, reagents or components for enriching or concentrating the pathogen may be provided to the sample processing device via a cartridge. For example, the cartridge may comprise an antibody-based capture surface for binding the pathogen, growth medium for culturing the pathogen, centrifugation vessels for centrifuging the pathogen, and a filter to capture the pathogens. Each of the reagents or components may be provided in the cartridge in separate, fluidically isolated vessels or chambers.

In embodiments provided herein, one or more portions of a sample 110 introduced into a sample processing device 100 may be used in one or more assays to test for response of a pathogen to one or more antimicrobials. To measure the growth of a pathogen in the presence of an antimicrobial, a microorganism growth medium and an antimicrobial may be provided within a sample processing device. In addition, a nucleic acid dye, metabolic indicator (such as resazurin), or other reagent may be provided to assay the growth of a pathogen in the presence of an antimicrobial. In embodiments, growth media may be introduced into a sample processing device via a cartridge which also contains a sample for processing in the device. In other embodiments, growth media may be introduced into a sample processing device separately from the introduction of a sample into the device. In embodiments, multiple different types of growth media may be introduced into a sample processing device, to support the growth of multiple different types of pathogens (e.g. 2, 3, 4, 5, 6, 7, 8, 9, 10, 15, 20, or more different types of growth media to support the growth of 2, 3, 4, 5, 6, 7, 8, 9, 10, 15, 20, or more different types of pathogens). In embodiments, multiple different separate fluidically isolated portions of a single type of growth medium may be introduced into a sample processing device (alone or in combination with other types of growth media). In embodiments, growth medium in a single vessel may be divided into two or more portions within a sample processing device, such as by a fluid handling system.

In embodiments, a growth medium introduced into a sample processing device may be pre-mixed with an antimicrobial for assaying the growth of a pathogen such that the antimicrobial is in the growth medium at the time of introduction of the growth medium into the sample processing device. In other embodiments, a growth medium does not contain an antimicrobial when the growth medium is introduced into a sample processing device, and then an antimicrobial is added to the growth medium within the sample processing device. For example, a growth medium may be introduced into a sample processing device via a cartridge, and the cartridge may contain the growth medium and antimicrobial in separate vessels. Once in the sample processing device, the antimicrobial and the growth medium may be mixed (e.g. a fluid handling system may bring the antimicrobial and the growth medium into fluid communication by aspirating the antimicrobial which is in liquid or suspended form, and then dispensing the antimicrobial into the growth medium, or the liquid growth medium may be aspirated and dispensed into a liquid or solid form of the antimicrobial). Further, the sample may be brought into fluid communication with the antimicrobial and the growth medium by the fluid handling system.

In embodiments, the growth medium introduced into a sample processing device may be pre-mixed with an antimicrobial and a metabolic indicator. In other embodiments, the growth medium is pre-mixed with an antimicrobial, and the metabolic indicator is added to the growth medium in the sample processing device. In other embodiments, a growth medium does not contain an antimicrobial or a metabolic indicator when the growth medium is introduced into a sample processing device, but the antimicrobial and the metabolic indicator are added to the growth medium in the sample processing device. For example, a cartridge may contain a growth medium, antimicrobial, and metabolic indicator in separate vessels. Once in the sample processing device, the antimicrobial, growth medium, and metabolic indicator may be mixed by the fluid handling system. In another example, the antimicrobial and growth medium are in the same vessel in a cartridge. In yet another example, the antimicrobial, growth medium, and metabolic indicator are in the same vessel in a cartridge. Further, the sample may be brought into fluid communication with the antimicrobial, growth medium, and metabolic indicator by the fluid handling system.

In some embodiments, multiple different antimicrobials may be introduced into a sample processing device, such that different antimicrobials may be introduced into a growth medium as desired. For example, a cartridge carrying a growth medium and a first antimicrobial and a second antimicrobial may be introduced into a sample processing device. Once in the sample processing device, based on a protocol selected for the pathogen or antimicrobial resistance to be tested, either the first antimicrobial or second antimicrobial may be combined with the growth medium. Thus, according to embodiments provided herein, different antimicrobials may be mixed-and-matched with different growth media within sample processing devices provided herein according to various different processing objectives for a sample or a pathogen therein.

For example, with embodiments provided herein, a protocol may be provided to the controller of a sample processing device which contains a growth medium and a first antimicrobial and a second antimicrobial, wherein the protocol contains instructions for a fluid handling system (e.g. an automated pipette) with the sample processing device to mix either the first antimicrobial or the second antimicrobial with the growth medium, depending on a pathogen identified in a sample and/or the antimicrobial of interest to test against the pathogen. In embodiments, a pathogen may be assessed for growth in the presence of an antimicrobial without moving the pathogen from its original sample to a separate growth medium. In such examples, an antimicrobial may be directly mixed with a sample containing a pathogen, and the response of the pathogen to the antimicrobial may be subsequently assessed. Any description herein to assessing the growth of a pathogen in a growth medium containing an antimicrobial may also apply to conditions where the antimicrobial is directly introduced into a sample containing a pathogen, unless the context clearly dictates otherwise. If growth of a virus in response to an antimicrobial is to be assessed, typically, the growth medium for the virus contains host cells in which the virus can replicate.

In embodiments, a sample which may contain a pathogen may be processed in a sample processing device for one or more markers which indicate if the sample contains at least one type of organism from a class of potential pathogens, such as bacteria, viruses, fungi, parasites, or protists. For example, a sample may be assayed in the sample processing device for a bacterial marker, such as the 16S rRNA, 23S rRNA, rpoB, gyrB, dnaK, amoA, and mip gene, or its gene product. In another example, a sample may be assayed for a fungal marker, such as the internal transcribed spacer (ITS) region of the ribosomal cistron. The one or more markers may be detected by nucleic acid amplification, a nucleic acid probe-based assay, or any other suitable assay in the sample processing device. In an embodiment, a reagent for the nucleic acid amplification reaction and/or a reagent for the nucleic acid probe-based assay may be provided in a cartridge. The cartridge may also contain the sample in a separate, fluidically isolated vessel. The reagent(s) and sample may be introduced into the sample processing device by inserting the cartridge into the sample processing device. In an embodiment, a fluid handling system of the sample processing device transfers a sample, or a portion thereof, into fluid communication with a reagent for the nucleic acid amplification and/or a nucleic acid probe-based assay. The mixture may then be incubated under conditions sufficient to support the amplification of a nucleic acid of the pathogen in the sample, or incubated under conditions sufficient to support hybridization of a nucleic acid probe to a nucleic acid of the pathogen in the sample.

A sample processing device that performs nucleic acid amplification or a nucleic acid probe-based assay may contain one or more hardware components for facilitating the performance of nucleic acid assays, such as a thermal control unit. The thermal control unit may maintain a selected temperature or range or cycle of temperatures in order to perform or support a nucleic acid assay (e.g., to thermocycle for a PCR assay or to maintain a selected constant temperature for an isothermal assay or a nucleic acid probe-based assay). The sample processing device may further contain one or more detectors or sensors for monitoring the nucleic acid assays and may also be used to measure non-nucleic acid assays (e.g. general chemistry assays, immunoassays, metabolic assays, etc.).

In other embodiments, to assay a pathogen for cell division, DNA replication, or other characteristic of the pathogen, pathogens may be moved by a fluid handling system within the device to a cytometer within the sample processing device, wherein the sample cytometer includes a microscopy stage which may receive a microscope slide. In embodiments, a sample is provided to a cartridge containing the microscope slide, and the cartridge is inserted into the sample processing device. The pathogens may then be introduced onto the microscope slide within the sample processing device.

In embodiments, with systems and methods provided herein, markers indicative of cell death, such as the expression of one or more biochemical markers in a cell, changes in chromosome structure, or the development of a particular cell morphology, may be measured as discussed above. The sample may be contacted with an antimicrobial, and the pathogen may assessed for one or more markers of cell death at one or more time intervals after the introduction of the antimicrobial to the sample. In embodiments, the one or more markers of cell death may be detected by staining a pathogen that been exposed to a particular antimicrobial and imaged in the sample processing device. In embodiments, a sample may be provided to a cartridge containing a stain and the cartridge inserted into the sample processing device containing an image capture device, such as a charge-coupled device (CCD) camera or CMOS sensor. In embodiments, the staining and imaging of the sample is automated within the sample processing device.

In embodiments, multiple different reagents for the detection or identification of a pathogen in a sample may be provided to sample processing device. Such multiple different reagents may be provided to a sample processing device, for example, in a cartridge which also contains a sample for processing. For example, within a single cartridge, any number and combination of the following types of reagents may be provided: a) a primer pair (i.e. containing a first primer and a second primer) for a nucleic acid amplification reaction to detect the presence of a specific nucleic acid from a pathogen, and to thereby indicate the presence of the pathogen in the sample; b) a primer pair for a nucleic acid amplification reaction to detect the presence of a specific antimicrobial resistance gene in a pathogen, and to thereby indicate the presence of the antimicrobial resistance gene in the sample; c) a primer pair for a nucleic acid amplification reaction to detect the presence of a specific antimicrobial resistance mutation in a pathogen (e.g. a point mutation in a gene), and to thereby indicate the presence of the antimicrobial resistance mutation in the sample; d) a primer pair for a nucleic acid amplification reaction to detect a nucleic acid sequence indicative of a class of microorganism (e.g. bacterial, viral, or fungal), and to thereby indicate the presence of a microorganism of a general class of microorganisms in the sample; e) a nucleic acid probe specific for a target nucleic acid of a pathogen for use in a nucleic acid probe-based assay to determine the presence of the pathogen in the sample; f) a nucleic acid probe specific for an antimicrobial resistance gene in a pathogen for use in a nucleic acid probe-based assay to determine the presence of an antimicrobial resistance gene in the pathogen; g) a nucleic acid probe specific for an antimicrobial resistance mutation in a pathogen (eg. a point mutation in a gene) for use in a nucleic acid probe-based assay to detect the presence of the antimicrobial resistance mutation; h) a nucleic acid probe specific for a nucleic acid sequence indicative of a class of microorganism (eg. bacterial, viral, or fungal) for use in a nucleic acid probe-based assay to detect the presence of a class of microorganism; i) a growth medium for a pathogen of interest; j) an antimicrobial, such that a pathogen may be provided with an opportunity to grow in the growth medium in the presence of the antimicrobial, in order to determine the response of the pathogen to the antimicrobial; k) a nucleic acid dye (eg., Hoechst dye, DAPI, ethidium bromide, SYBR dye); and l) a metabolic indicator (eg. resazurin, CTC, CFDA-SE, and luciferin) for detecting growth of a pathogen in the presence of an antimicrobial. Moreover, in embodiments, multiple numbers (e.g. 2, 3, 4, 5, 6, 7, 8, 9, 10, or more) of any of the above reagents may be provided to a sample processing device, and such reagents may be different primers, probes, antimicrobials, growth medium, etc. In an embodiment, all reagents necessary for a particular assay may also be provided to a sample processing device via a cartridge as described herein. In an embodiment, each of the reagents may be in separate fluidically isolated vessels in a cartridge. In another embodiment, any number or combination of reagents may be in the same vessel in a cartridge.

With systems and methods provided herein, a sample may be assessed for a pathogen, and in embodiments, 1, 2, 3, or all 4 of the following characteristics of a potential pathogen in the sample may be assessed: a) a class of pathogen (e.g. bacterial, viral, or fungal) which is present in a sample; b) a particular species, sub-species, or strain of pathogen which is in a sample; c) the growth response of a pathogen in a sample to an antimicrobial; or d) if a sample or pathogen therein contains an antimicrobial-resistance gene or antimicrobial-resistance mutation. Moreover, a sample may be assayed for different classes of pathogens or different species, sub-species, or strains of pathogens, and a pathogen may be assayed for response to different antimicrobials or antimicrobial resistance genes. In embodiments, any or all of the assays may be performed within a housing of a single sample processing device. In other embodiments, the assays may be performed by more than one sample processing device.

In embodiments, a feedback loop may permit reflex testing which may cause subsequent assays, preparation steps, and/or other processes to be initiated after starting or completing another assay within the systems, devices, and methods provided herein. Such subsequent assays, preparation steps, and/or other processes may be initiated automatically without any human intervention. Optionally, reflex testing is performed in response to a first assay result. For example, a cartridge may be pre-loaded with reagents for a first assay to detect the presence of a pathogen in a sample (eg. reagents for a nucleic acid amplification reaction to detect a nucleic acid of a pathogen) and reagents for a second assay to determine antimicrobial resistance or susceptibility of a pathogen (eg. antimicrobials, microorganism growth medium, and metabolic indicator). If the result of the first assay indicates that a pathogen is present in the sample, the second assay is run with the same sample in the device. The device protocol is planned to account for the possibility of running the reflex test. Some or all protocol steps of the second assay may be initiated or performed before the first assay is complete. For example, culturing of the sample in a microorganism growth medium in the presence of an antimicrobial may be initiated before an assay for detecting the presence of a pathogen is completed.

In embodiments, a sample may be assessed for a panel of pathogens which may be present in the sample, and one or more antimicrobial-resistance traits which may be present in one or more pathogens in the panel. For example, a sample may be tested for multiple sexually-transmitted disease pathogens, and the sample may also be assessed for the response of one or more of such pathogens to one or more antimicrobials. Other examples of panels which may be tested according to systems and methods provided herein include a hospital-acquired infection panel (e.g. MRSA), or a tropical disease pathogen panel. In embodiments, a subject could be tested for one or more pathogens or a panel of pathogens before a subject is admitted into a patient care location (e.g. hospital or clinic), and in addition or separately tested for one or more pathogens or a panel of pathogens once being admitted into a patient care location. Systems and methods provided herein may be used to continuously monitor a patient for infection, and thus may be used to improve care of a patient at a care location or in the patient's home. For example, if a patient is determined to be suffering from an infection with a pathogen which is susceptible to a particular antimicrobial, the patient can be administered the antimicrobial. In certain embodiments, for example, if a patient is suffering from an infection but also necessitates surgery, an object (such as a patch) which may be used during the surgery or implanted into the subject during surgery can be pre-coated or otherwise incorporated with an antimicrobial which will impair the growth of the infection-causing pathogen.

In embodiments, a sample processing device may be configured to transmit data obtained from a sample. In embodiments, a sample processing device may be configured to communicate over a network. A sample processing device may include a communication module that may interface with the network. A sample processing device may be connected to the network via a wired connection or wirelessly. The network may be a local area network (LAN) or a wide area network (WAN) such as the Internet. In some embodiments, the network may be a personal area network. The network may include the cloud. The sample processing device may be connected to the network without requiring an intermediary device, or an intermediary device may be required to connect a sample processing device to a network. A sample processing device may communicate over a network with another device, which may be any type of networked device, including but not limited to a personal computer, server computer, or laptop computer; personal digital assistants (PDAs) such as a Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Such communication may include providing data to a cloud computing infrastructure or any other type of data storage infrastructure which may be accessed by other devices.

A sample processing device may provide data regarding a sample to, e.g., a health care professional, a health care professional location, such as a laboratory, or an affiliate thereof. One or more of a laboratory, health care professional, or subject may have a network device able to receive or access data provided by the sample processing device. A sample processing device may be configured to provide data regarding a sample to a database. A sample processing device may be configured to provide data regarding a sample to an electronic medical records system, to a laboratory information system, to a laboratory automation system, or other system or software. A sample processing device may provide data in the form of a report.

A laboratory, device, or other entity or software may perform analysis on data regarding a sample in real-time. Analysis may include qualitative and/or quantitative evaluation of a sample. Data analysis may include a subsequent qualitative and/or quantitative evaluation of a sample. Optionally, a report may be generated based on raw data, pre-processed data, or analyzed data. Such a report may be prepared so as to maintain confidentiality of the data obtained from the sample, the identity and other information regarding the subject from whom a sample was obtained, analysis of the data, and other confidential information. The report and or the data may be transmitted to a health care professional. Data obtained by a sample processing device, or analysis of such data, or reports, may be provided to a database, an electronic medical records system, to a laboratory information system, to a laboratory automation system, or other system or software.

In embodiments, use of systems and methods provided herein may decrease the need for use of a central venous catheter ("central line") in patients. In some situations, a central line may be maintained in a patient at least in part due to a need for regularly obtaining relatively large blood samples from the patient. The presence of a central line in a patient may be undesirable, for example, as it may increase the risk of the patient developing one or more infections, such as with *Staphylococcus aureus* or *Staphylococcus epidermidis*. By use of systems and methods provided herein to process small volume samples from a subject, it may be possible to not use a central line in certain patients. For example, instead of obtaining a relatively large volume of blood for analysis from the patient through the central line, a small volume of blood may be obtained through an alternative site (e.g. a finger), and that small volume of blood may be used for analysis with systems and method provided herein. In embodiments, methods provided herein may be performed using a sample which is not obtained via a central line in a patient. In embodiments, samples for use with a system or method provided herein may be collected from a patient at least 1, 2, 3, 4, 5, 6, 7, 8, 9, 10, 11, 12, 15, or 20 times in a 24 hour period, wherein none of the samples are obtained via a central line in the patient. In embodiments, at least 1, 2, 3, 4, 5, 6, 7, 8, 9, 10, 11, 12, 15, or 20 samples may be collected in a 24 hour period and used with a system or method provided herein, wherein none of the samples are obtained via a central line in the patient.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. For example, a feature of one embodiment may be combined with a feature of another embodiment, whether such combination is described herein or not. It should also be understood that while the invention provided herein has been described herein using a limited number of terms and phrases for purposes of expediency, the invention could also be described using other terms and phrases not provided herein which also accurately describe the invention.

It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. The appended claims are not to be interpreted as including means-plus-function limitations, unless such a limitation is explicitly recited in a given claim using the phrase "means for." As used in the description herein and through the claims that follow, a first object described as containing "at least a portion" of a second object may contain the full amount of/the complete second object.

As used in the description herein and throughout the claims that follow, the terms "comprise", "include", and "contain" and related tenses are inclusive and open-ended, and do not exclude additional, unrecited elements or method steps. Also, the presence of broadening words and phrases such as "one or more," "at least," "but not limited to" or other like phrases in some instances shall not be read to mean that the narrower case is intended or required in instances where such broadening phrases may be absent. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

This document contains material subject to copyright protection. The copyright owner (Applicant herein) has no objection to facsimile reproduction by anyone of the patent documents or the patent disclosure, as they appear in the US Patent and Trademark Office patent file or records, but otherwise reserves all copyright rights whatsoever. The following notice shall apply: Copyright 2014-15 Theranos, Inc.

The following examples are offered for illustrative purposes only, and are not intended to limit the present disclosure in any way.

EXAMPLES

Example 1

Resazurin Reduction Method for Detecting Antimicrobial Resistance or Susceptibility A single *E. coli* bacterial colony (*E. coli* K12 MG1655) known to be resistant to kanamycin and a single *E. coli* bacterial colony (*E. coli* K12 MG1655) known to be resistant to carbenicillin were separately cultured in LB media for 12-15 hrs until the bacterial cells were in mid-log phase (about $10^8$ cells/ml). The culture was then serial diluted to $5\times10^2$, $5\times10^3$, $5\times10^4$, and $5\times10^5$ cells in LB media containing either 50 µg/ml kanamycin or 100 µg/ml carbenicillin. Resazurin was added to each dilution at a final concentration of 20, 40, or 80 µM in a total reaction volume of 100 µl. Each diluted culture was cultured at 37° C. and fluorescence was measured at wavelength 590 nm at 0, 1, 2, 3, 4, 5, and 6 hrs from the start of culture in the presence of the antibiotic.

Figure 5A:
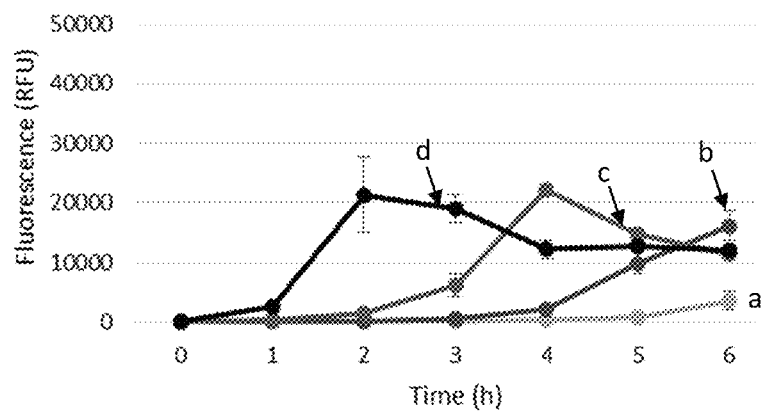
FIGS. 5A-5F show growth characteristics of a kanamycin resistant E. coli K12 MG1655 strain in kanamycin (FIGS. 5A-5C) or carbenicillin (FIGS. 5D-5F) and resazurin at final concentrations of 20 µM (FIGS. 5A and 5D), 40 µM (FIGS. 5B and 5E), or 80 µM (FIGS. 5C and 5F) in a total reaction volume of 100 µl as measured by detecting fluorescence at 590 nm at times 0, 1, 2, 3, 4, 5, and 6 hrs from the initiation of culture with the antibiotic and resazurin. Growth characteristics of the culture initiated at bacterial cell concentrations of $5 \times 10^2$ cells/total reaction volume (a), $5 \times 10^3$ cells/total reaction volume (b), $5 \times 10^4$ cells/total reaction volume (c), and $5 \times 10^5$ cells/total reaction volume (d) are shown.
Figure 5B:
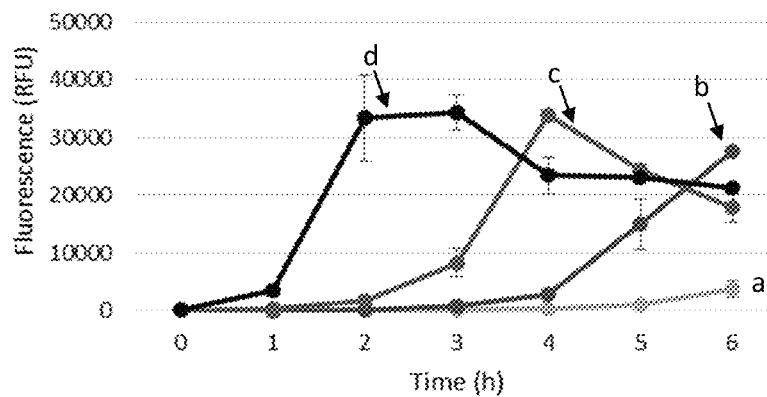
Figure 5C:
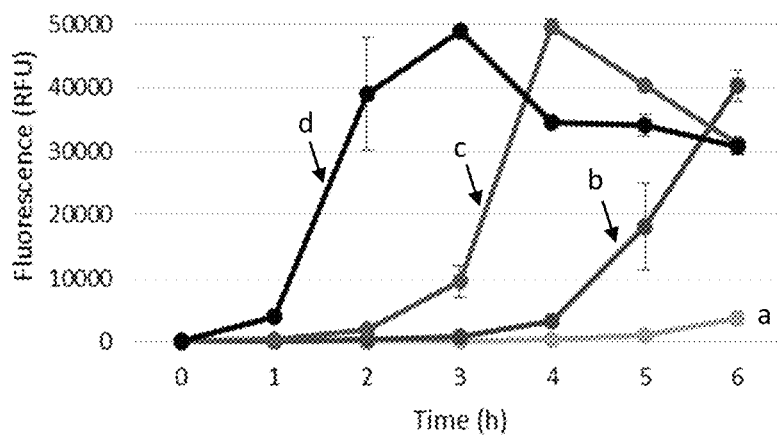
Figure 5D:
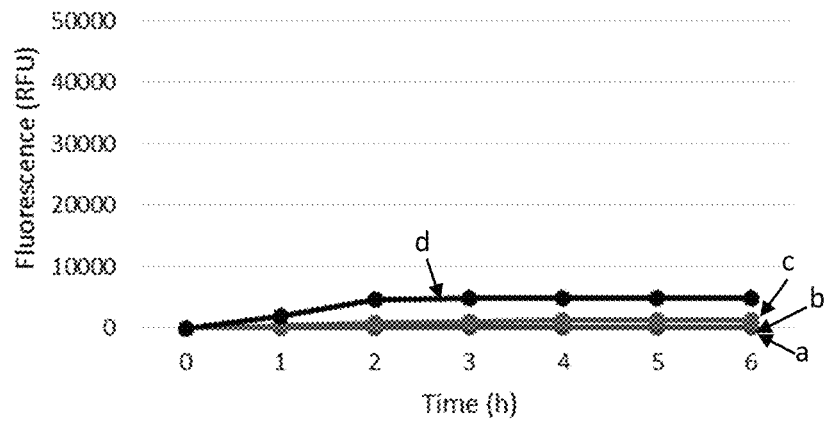
Figure 5E:
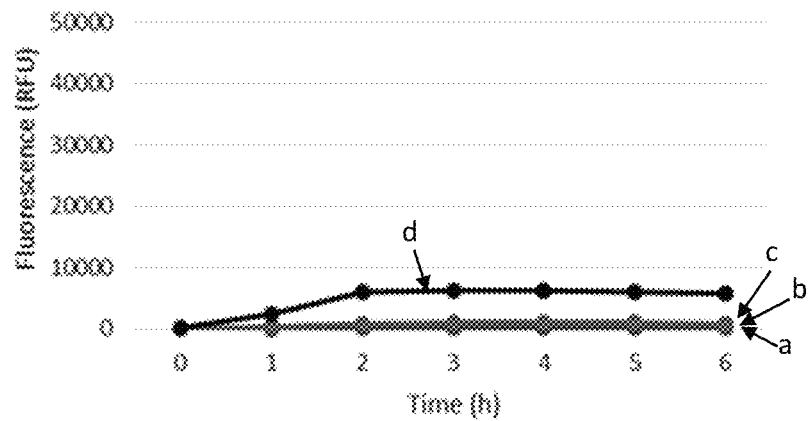
Figure 5F:
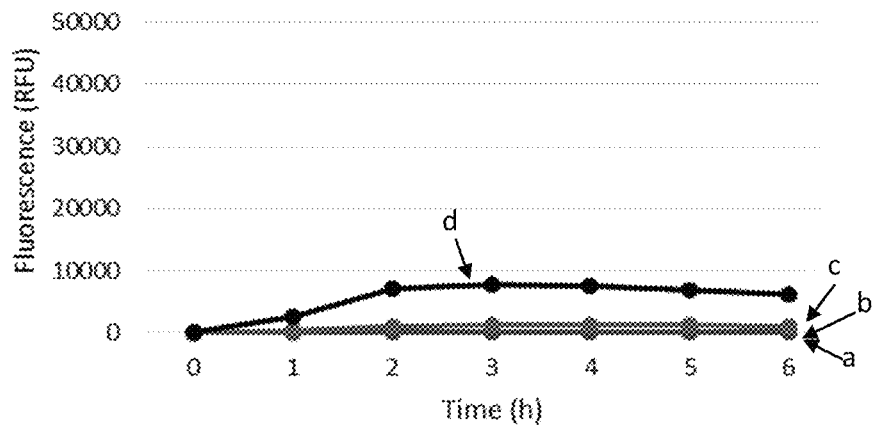

FIGS. 5A-5C show that the kanamycin resistant strain exhibited growth at all cell concentrations in the presence of kanamycin and in all resazurin concentrations. The higher initial cell concentrations (eg. at $5\times10^3$, $5\times10^4$, and $5\times10^5$ cells) exhibited faster growth in the presence of kanamycin and thus, resistance to the antibiotic could be detected within 1-5 hrs of initiating the culture. The lower initial cell concentration (at $5\times10^2$ cells) began showing resistance to the antibiotic at about 6 hrs after initiating the culture. In contrast, FIGS. 5D-5F show that the kanamycin resistant strain exhibited slow or no growth in the presence of carbenicillin at each cell concentration in all resazurin concentrations.

Figure 6A:
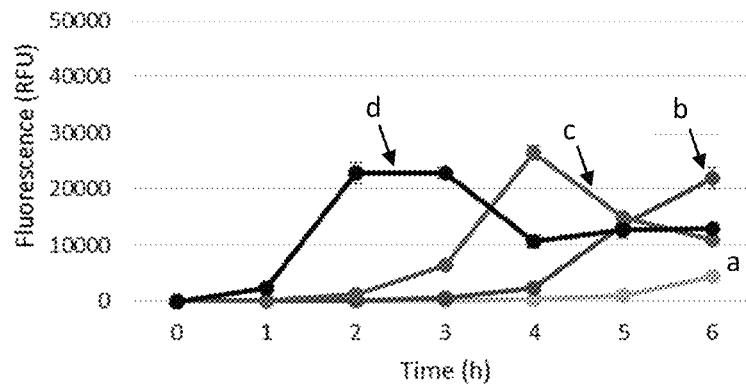
FIGS. 6A-6F show growth characteristics of a carbenicillin resistant E. coli K12 MG1655 strain in carbenicillin (FIGS. 6A-6C) or kanamycin (FIGS. 6D-6F) and resazurin at final concentrations of 20 µM (FIGS. 6A and 6D), 40 µM (FIGS. 6B and 6E), or 80 µM (FIGS. 6C and 6F) in a total reaction volume of 100 µl as measured by detecting fluorescence at 590 nm at times 0, 1, 2, 3, 4, 5, and 6 hrs from the initiation of culture with the antibiotic and resazurin. Growth characteristics of the culture initiated at bacterial cell concentrations of $5 \times 10^2$ cells/total reaction volume (a), $5 \times 10^3$ cells/total reaction volume (b), $5 \times 10^4$ cells/total reaction volume (c), and $5 \times 10^5$ cells/total reaction volume (d) are shown.
Figure 6B:
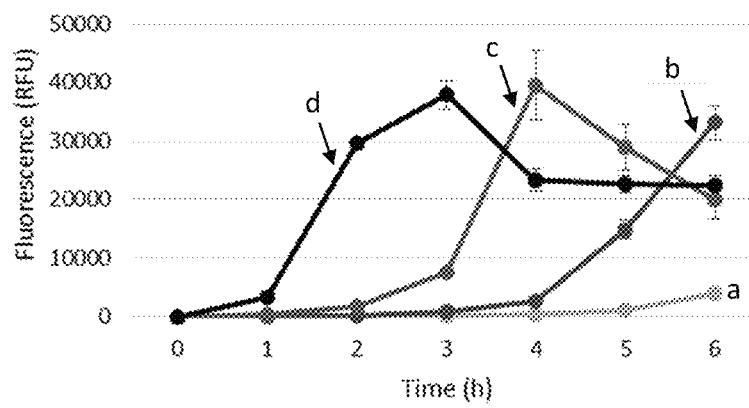
Figure 6C:
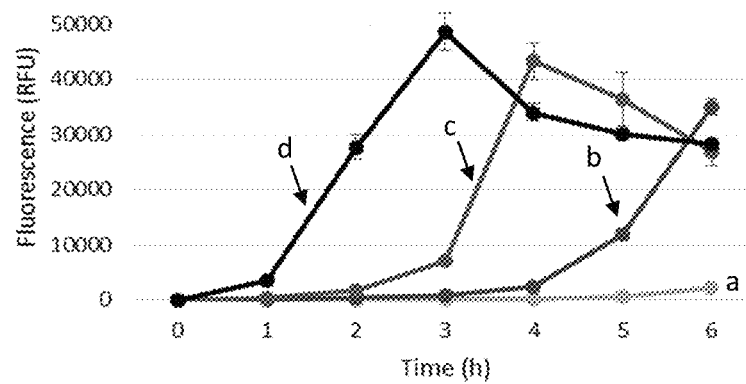
Figure 6D:
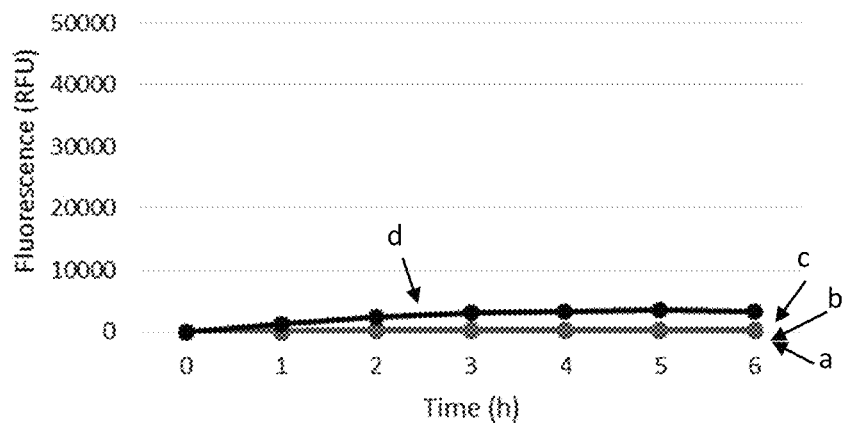
Figure 6E:
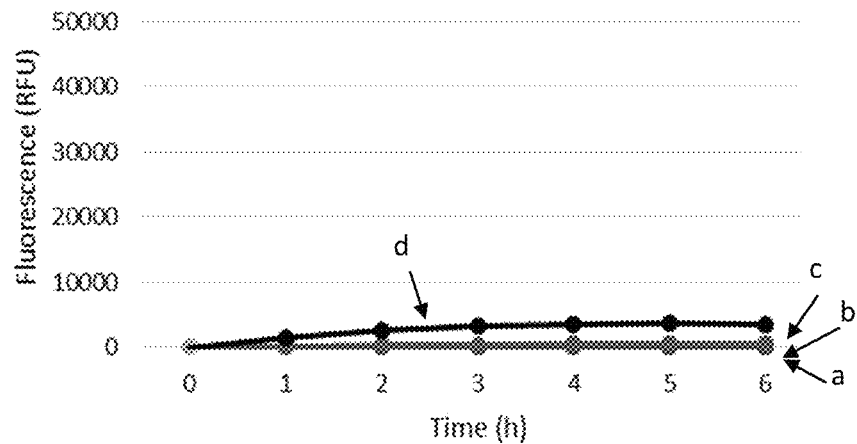
Figure 6F:
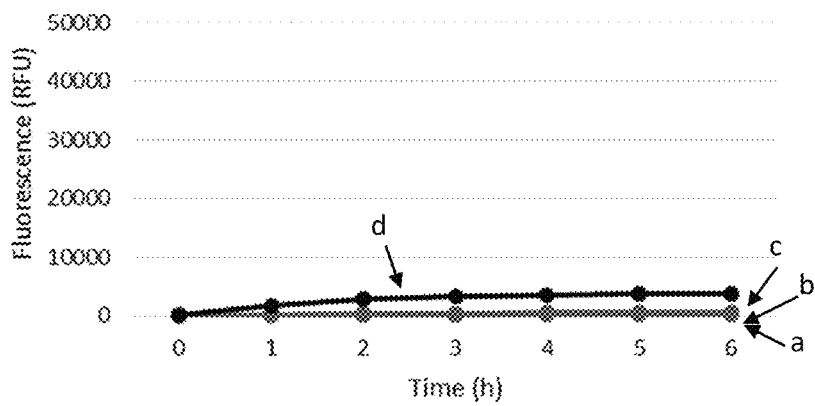

FIGS. 6A-6C show that the carbenicillin resistant strain exhibited growth at all cell concentrations in the presence of carbenicillin and in all resazurin concentrations. The higher initial cell concentrations (eg. at $5\times10^3$, $5\times10^4$, and $5\times10^5$ cells) exhibited faster growth in the presence of carbenicillin and thus, resistance to the antibiotic could be detected within 1-5 hrs of initiating the culture. The lower initial cell concentration (at $5\times10^2$ cells) began showing resistance to the antibiotic at about 6 hrs after initiating the culture. In contrast, FIGS. 6D-6F show that the carbenicillin resistant strain exhibited slow or no growth in the presence of kanamycin at each cell concentration in all resazurin concentrations.

Example 2

Resazurin Reduction Method in a Small Reaction Volume

The resazurin reduction method was repeated using the kanamycin resistant strain but in a 10 µl total reaction volume and with final cell concentrations of $5\times10^1$, $5\times10^2$, $5\times10^3$, and $5\times10^4$ cells per reaction. The same final resazurin concentrations (20, 40, or 80 µM), kanamycin concentration, and carbenicillin concentration were used as above. Fluorescence was measured at wavelength 590 nm at 0, 1, 2, 3, 4, 5, 6, and 7 hrs from the start of culture in the presence of the antibiotic.

Figure 7A:
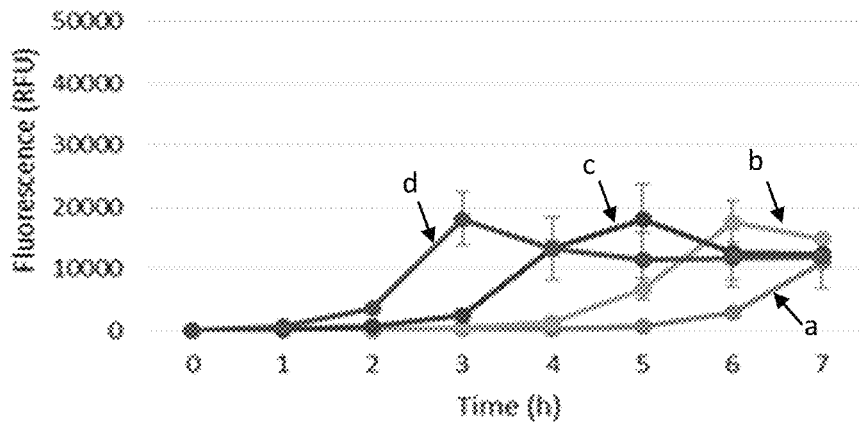
FIGS. 7A-7F show growth characteristics of a kanamycin resistant E. coli K12 MG1655 strain in kanamycin (FIGS. 7A-7C) or carbenicillin (FIGS. 7D-7F) and resazurin at final concentrations of 20 µM (FIGS. 7A and 7D), 40 µM (FIGS. 7B and 7E), or 80 µM (FIGS. 7C and 7F) in a total reaction volume of 10 µl as measured by detecting fluorescence at 590 nm at times 0, 1, 2, 3, 4, 5, 6, and 7 hrs from the initiation of culture with the antibiotic and resazurin. Growth characteristics of the culture initiated at bacterial cell concentrations of $5 \times 10^1$ cells/total reaction volume (a), $5 \times 10^2$ cells/total reaction volume (b), $5 \times 10^3$ cells/total reaction volume (c), and $5 \times 10^4$ cells/total reaction volume (d) are shown.
Figure 7B:
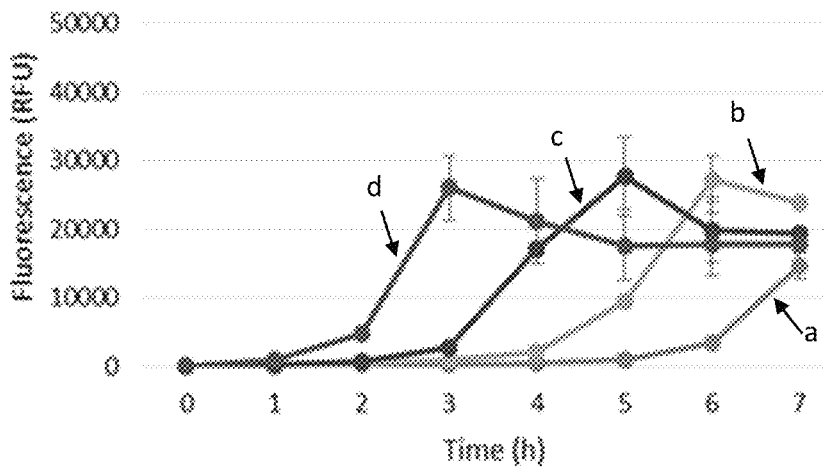
Figure 7C:
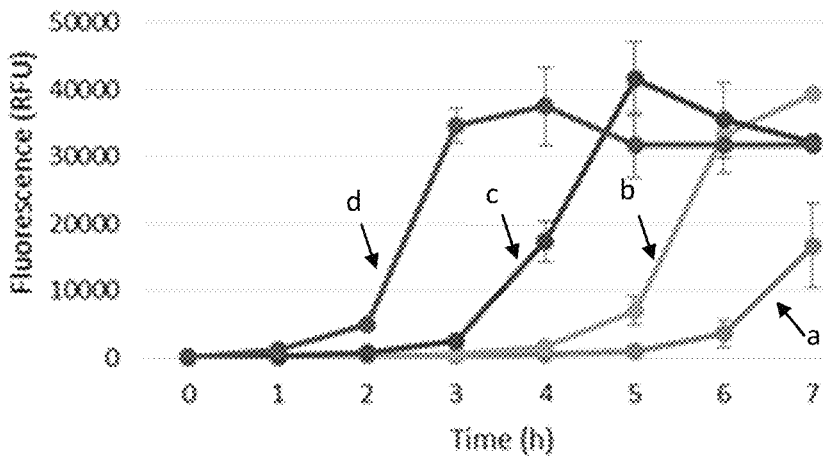
Figure 7D:
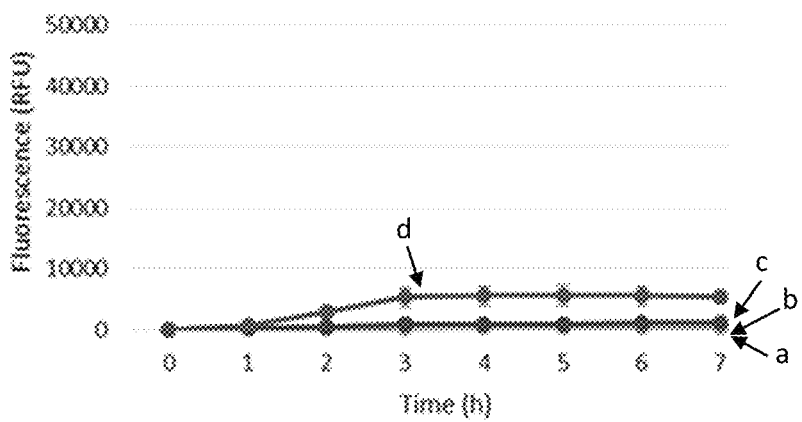
Figure 7E:
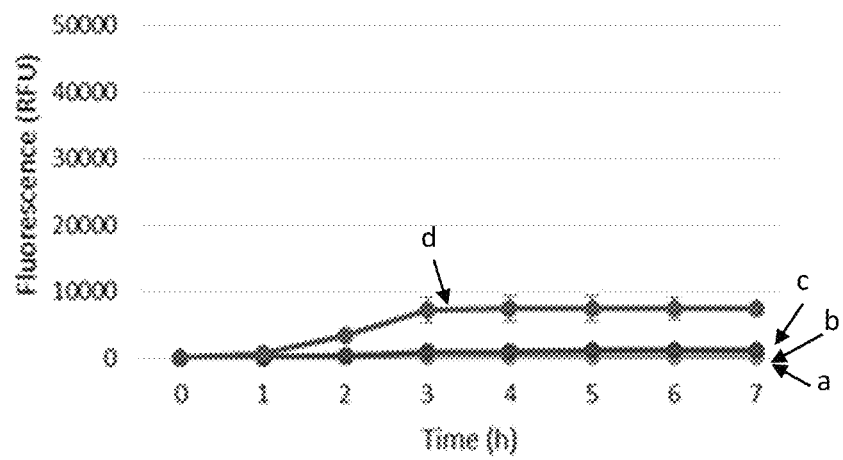
Figure 7F:
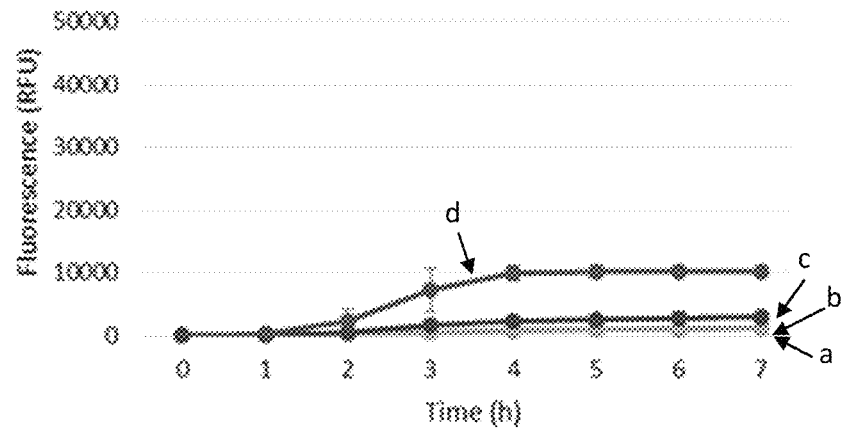

As shown in FIGS. 7A-7C, the kanamycin resistant strain exhibited growth at all cell concentrations in the presence of kanamycin and in all resazurin concentrations. The higher initial cell concentrations (eg. at $5\times10^2$, $5\times10^3$, and $5\times10^4$ cells) exhibited faster growth in the presence of kanamycin and thus, resistance to the antibiotic could be detected within 1-6 hrs of initiating the culture. The lower initial cell concentration (at $5\times10^1$ cells) began showing resistance to the antibiotic at about 7 hrs after initiating the culture. In contrast, FIGS. 7D-7F show that the kanamycin resistant strain exhibited slow or no growth in the presence of carbenicillin at each cell concentration in all resazurin concentrations.

Accordingly, the resazurin reduction assay can be used to detect antimicrobial resistance/susceptibility with a small amount of sample (eg. 10-100 µl) containing low copy numbers of a pathogen (eg. $10^1$-$10^5$ cells) and in a short time (eg. within 1-7 hrs of initiating culture in the presence of the antimicrobial). Moreover, the resazurin reduction assay does not require lyisng the cells and can be performed at 37° C. Thus, the resazurin reduction assay is a convenient and fast assay for determining the resistance or susceptibility of a pathogen to an antimicrobial.

The invention claimed is:

1. A method for analysis of a sample, the method comprising:
   receiving a cartridge in a sample processing device, wherein the sample processing device comprises a fluid handling system, and wherein the cartridge comprises:
   a sample,
   an antimicrobial,
   a microorganism growth medium, and
   a reagent for a nucleic acid amplification reaction;
   transferring, by the fluid handling system, a first portion of the sample from a first region of the cartridge to a second region of the cartridge in fluid communication with the reagent for the nucleic acid amplification reaction, to generate a first mixture comprising the first portion of the sample and the reagent for the nucleic acid amplification reaction;
   transferring, by the fluid handling system, a second portion of the sample from the first region of the cartridge to a third region of the cartridge fluid communication with the antimicrobial and the microorganism growth medium, to generate a second mixture comprising the second portion of the sample, the antimicrobial, and the microorganism growth medium;
   incubating the first mixture under conditions sufficient to support the amplification of a nucleic acid of the pathogen in the sample;
   culturing the second mixture under conditions sufficient to support growth of the pathogen in the second mixture;
   detecting amplification of the nucleic acid from the pathogen in the sample; and
   detecting growth of the pathogen in the sample.

2. The method of claim 1, wherein detecting amplification of the nucleic acid from the pathogen in the sample comprises detecting fluorescence from a dye in the first mixture.

3. The method of claim 1, wherein the detecting amplification of the nucleic acid from the pathogen in the sample and the detecting of the growth of the pathogen in the sample both occur no more than 24 hours after the cartridge is received in the sample processing device.

4. A method for analysis of a sample, the method comprising:
   receiving a cartridge in a sample processing device, wherein the sample processing device comprises a fluid handling system, and wherein the cartridge comprises:
   a sample,
   an antimicrobial,
   a microorganism growth medium; and
   a nucleic acid probe capable of specifically hybridizing to a nucleic acid, or a complement thereof, of the pathogen;
   transferring, by the fluid handling system, a first portion of the sample from a first region of the cartridge to a second region of the cartridge in fluid communication with the nucleic acid probe, to generate a first mixture comprising the first portion of the sample and the nucleic acid probe;
   transferring, by the fluid handling system, a second portion of the sample from the first region of the cartridge to a third region of the cartridge in fluid communication with the antimicrobial and the microorganism growth medium, to generate a second mixture comprising the second portion of the sample, the antimicrobial, and the microorganism growth medium;
   incubating the first mixture under conditions sufficient to specifically hybridize to a nucleic acid, or a complement thereof, of the pathogen in the sample;
   culturing the second mixture under conditions sufficient to support growth of the pathogen;
   detecting the nucleic acid of the pathogen in the sample; and
   detecting growth of the pathogen in the sample.

5. The method of claim 4, wherein detecting growth of the pathogen in the sample comprises examining the second mixture with a cytometer.

6. The method of claim 5, wherein examining comprises counting the number of pathogen cells.

7. The method of claim 5, wherein examining comprises detecting an antigen of the pathogen.

8. The method of claim 5, wherein examining comprises determining a ratio or number of pathogen cells undergoing cell division.

9. The method of claim 4, wherein detecting growth of the pathogen in the sample comprises examining the second mixture with a spectrophotometer.

10. The method of claim 9, wherein examining comprises determining the optical density of the second mixture.

11. The method of claim 10, wherein the method comprises:
  transferring, by the fluid handling system, the second portion of the sample into fluid communication with the antimicrobial, the microorganism growth medium, and a metabolic indicator, configured to be metabolized to produce a metabolic product, to generate a second mixture comprising the second portion of the sample, the antimicrobial, the microorganism growth medium, and the metabolic indicator.

12. The method of claim 11, wherein the metabolic indicator is selected from resazurin, 5-cyano-2,3-ditolyl tetrazolium chloride (CTC), carboxyfluorescein diacetate succinimidyl ester (CFDA-SE), and luciferin.

13. The method of claim 12, wherein the metabolic indicator is resazurin.

* * * * *